(12) United States Patent
Charlesworth et al.

(10) Patent No.: US 11,109,638 B2
(45) Date of Patent: Sep. 7, 2021

(54) ORTHOTIC AND A METHOD OF MAKING AN ORTHOTIC

(71) Applicant: PEACOCKS ORTHOTICS LIMITED, Newcastle upon Tyne (GB)

(72) Inventors: Iain Charlesworth, Northumberland (GB); Chris Pluse, Tyne and Wear (GB); David Eardley, Northumberland (GB); Leigh Wallace, Tyne and Wear (GB); Jari Pallari, Tyne and Wear (GB)

(73) Assignee: PEACOCKS ORTHOTICS LIMITED, Newcastle Upon Tyne (GB)

( * ) Notice: Subject to any disclaimer, the term of this patent is extended or adjusted under 35 U.S.C. 154(b) by 513 days.

(21) Appl. No.: 15/526,487

(22) PCT Filed: Sep. 11, 2015

(86) PCT No.: PCT/GB2015/052627
§ 371 (c)(1),
(2) Date: May 12, 2017

(87) PCT Pub. No.: WO2016/075429
PCT Pub. Date: May 19, 2016

(65) Prior Publication Data
US 2017/0318900 A1    Nov. 9, 2017

(30) Foreign Application Priority Data

Nov. 13, 2014  (GB) ...................................... 1420201
Apr. 7, 2015   (GB) ...................................... 1505819

(51) Int. Cl.
*B33Y 10/00*    (2015.01)
*A43B 7/14*     (2006.01)
(Continued)

(52) U.S. Cl.
CPC ................ *A43B 7/141* (2013.01); *A43B 7/14* (2013.01); *A43B 7/144* (2013.01); *A43B 7/1405* (2013.01);
(Continued)

(58) Field of Classification Search
CPC .. A43D 2200/60; A61B 5/107; A61B 5/1074; B29C 64/106; B29C 64/112;
(Continued)

(56) References Cited

U.S. PATENT DOCUMENTS

2015/0165690 A1    6/2015  Tow
2016/0101572 A1*   4/2016  Schouwenburg ..... B29C 64/386
                                                      700/98

FOREIGN PATENT DOCUMENTS

DE    102011055238    5/2013
GB       2508204      5/2014
(Continued)

OTHER PUBLICATIONS

Corresponding International Search Report for PCT/GB2015/052627, dated Feb. 2, 2016. WO.

*Primary Examiner* — Leo B Tentoni
(74) *Attorney, Agent, or Firm* — The Belles Group, P.C.

(57) ABSTRACT

A method of making an orthotic is disclosed. The method includes the steps of taking measurements relating to a foot and then creating a digital representation of an orthotic on a display device based on said measurements. This digital representation of the orthotic having a heel portion for supporting a heel of a person and a distal portion located in front of the heel portion which can be divided into first and second distal portions. The thickness of the digital representation of the first and second distal portions is then varied such that one of the distal portions is thicker than the other. Finally, an additive manufacturing technique, using a sub-
(Continued)

stantially uniform material or materials, is used to create a physical version of the digital representation of the orthotic.

12 Claims, 25 Drawing Sheets

(51) Int. Cl.
      *A43D 1/02*       (2006.01)
      *B33Y 80/00*       (2015.01)
      *A61F 5/14*       (2006.01)
      *B29C 64/106*       (2017.01)
      *B29C 64/112*       (2017.01)
      *B29D 35/12*       (2010.01)
      *B29C 64/386*       (2017.01)
      *B33Y 50/02*       (2015.01)
      *A43B 17/08*       (2006.01)
      *A61B 5/103*       (2006.01)
      *B33Y 50/00*       (2015.01)
      *A61B 5/107*       (2006.01)

(52) U.S. Cl.
CPC ............ *A43B 7/1475* (2013.01); *A43B 17/08* (2013.01); *A43D 1/02* (2013.01); *A43D 1/025* (2013.01); *A61B 5/1036* (2013.01); *A61F 5/14* (2013.01); *B29C 64/106* (2017.08); *B29C 64/112* (2017.08); *B29C 64/386* (2017.08); *B29D 35/122* (2013.01); *B29D 35/124* (2013.01); *B33Y 50/02* (2014.12); *B33Y 80/00* (2014.12); *A43D 2200/60* (2013.01); *A61B 5/1074* (2013.01); *B33Y 50/00* (2014.12)

(58) Field of Classification Search
CPC .. B29C 64/386; B29D 35/122; B29D 35/124; B33Y 10/00; B33Y 50/00; B33Y 80/00; A43B 7/1405
USPC ............ 264/40.1, 308; 73/172; 700/98, 119; 36/43
See application file for complete search history.

(56) References Cited

FOREIGN PATENT DOCUMENTS

WO       2014014977       1/2014
WO       WO-2014080217 A1 *       5/2014       ............... A61F 5/14

* cited by examiner

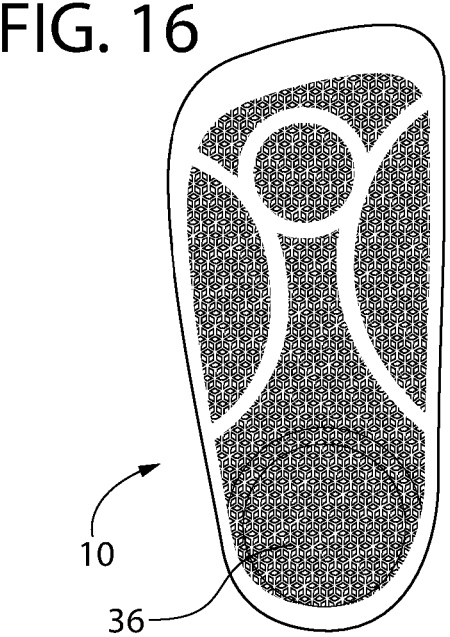
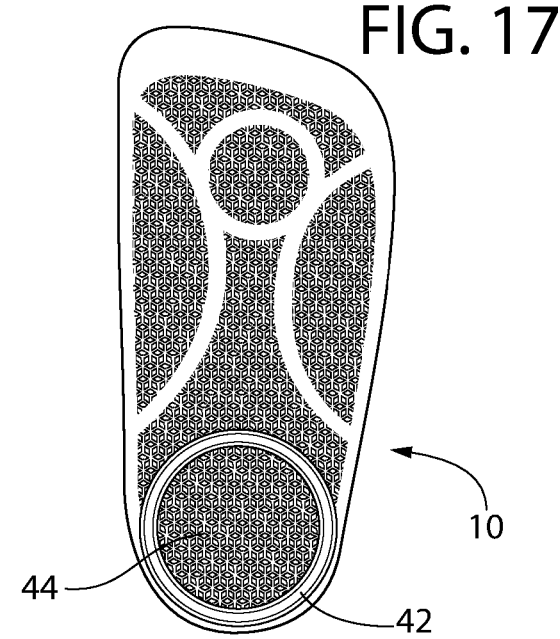
FIG. 16    FIG. 17
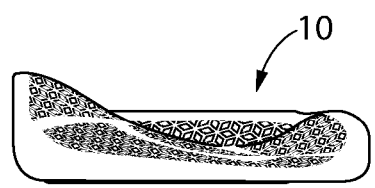
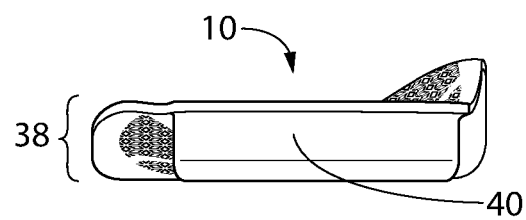
FIG. 18    FIG. 19
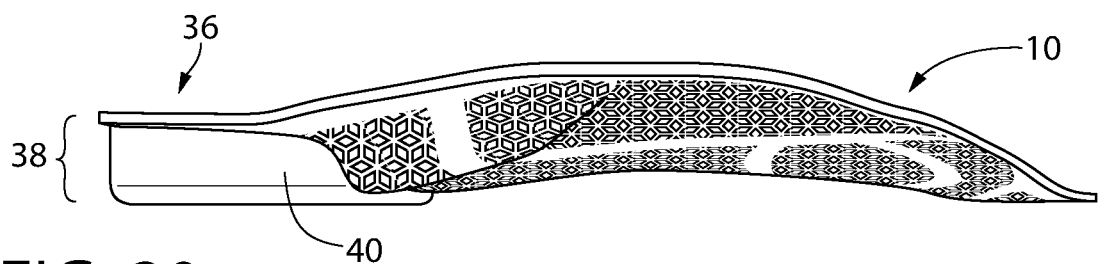
FIG. 20
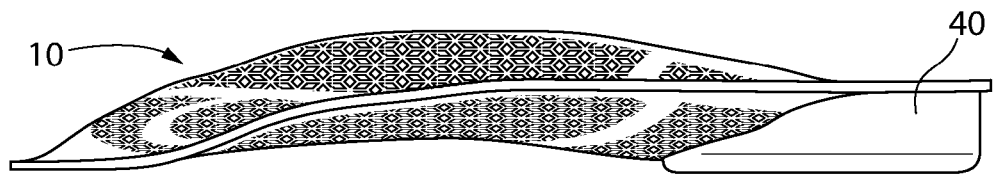
FIG. 21

ORTHOTIC AND A METHOD OF MAKING AN ORTHOTIC

The present application is a U.S. national stage entry under 35 U.S.C. § 371 of Patent Cooperation Treaty Patent Application No. PCT/GB2015/052627, filed Sep. 11, 2015, which claims priority to GB Patent Application No. 1505819.1, filed Apr. 7, 2015 and GB Patent Application No. 1420201.4, filed Nov. 13, 2014, the entireties of which are incorporated herein by reference.

The present invention relates to an orthotic and a method of making an orthotic and relates particularly, but not exclusively, to an orthopaedic insole for use in a shoe.

Foot orthotic devices, or orthopaedic insoles, are medical devices used to treat a number of patient pathologies, musculoskeletal problems, prevent these or enhance performance. For example, conditions such as plantar fasciitis, pressure lesions on the feet, pain from foot arthritis and conditions in the rest of the body that require the modifying of kinetics in the lower limb and feet can be successfully treated with foot orthoses.

A simple Foot Orthotic is a form-fitting insole that usually conforms to the foot on the superior side and can have a generic shoe-fitting shape on the inferior side. In some cases the Foot Orthotic device is a shell with a certain thickness with a heel element added.

They work by altering the kinematics of the forces acting through the foot and can for example, reduce the forces acting in another part of the body in the gait cycle by altering foot function. They can also be used to redistribute the pressure on the foot to reduce pathological forces or alter the centre of mass.

Foot orthotics utilise different materials in an attempt to treat patient pathologies. The variety of materials used includes carbon fibre, EVA, different gels and polypropylene. Most Foot Orthotic devices used are mass produced but bespoke Foot Orthotics are also made to treat the patient's issues in a more focussed and effective way.

Bespoke foot orthotics can be flexible, rigid or can have a mix of rigid and flexible sections. These are usually created by using different materials, such as hard plastic shells with a foam top cover. Such bespoke orthotics are difficult to create accurately to treat specific patient pathologies.

Foam devices wear out, are unhygienic and can be bulky and heavy, all characteristics undesirable to the patients. Milled and thermoplastic polypropylene devices can be bulky, heavy and too rigid. They also require top covers and additional materials to be glued onto the main body of the orthotic. These extra top covers, pads and the like, wear out requiring regular repairs.

Preferred embodiments of the present invention seek to overcome the above described disadvantages of the prior art.

According to an aspect of the present invention there is provided a method of making an orthotic, comprising the steps:—
taking measurements relating to a foot;
creating a digital representation of an orthotic on a display device based on said measurements, the orthotic having a heel portion for supporting a heel of a person and a distal portion located in front of said heel portion, said distal portion being divided into a first and a second distal portion;
varying the thickness of the digital representation of the first and second distal portions such that one of said first and second distal portions is thicker than the other of said first and second distal portions;
using additive manufacturing using a substantially uniform material or materials to create a physical version of the digital representation of the orthotic.

By varying the thickness and flexibility of the bespoke orthotic the advantage is provided of that pronation or supination of the foot can be encouraged by being more flexible on the medial or lateral portion of the orthotic. This pronation or supination alters the centre of mass in the transverse plane for therapeutic effect. For example, by creating an orthotic which is stiff laterally and more flexible medially this exerts a different ground reaction and applies a pronatory moment to encourage pronation. This in turn diverts the centre of mass medially and can be applied to cases of medial knee arthritis, peroneal dysfunction, medial impingement and other pathologies where excessive supination is the cause. Likewise, by creating an orthotic which is stiff laterally and more flexible medially this exerts the opposite ground reaction and applies a supinatory moment to encourage supination. This in turn diverts the centre of mass laterally and can be applied to cases of lateral knee arthritis and other pathologies which result from excessive pronation. Furthermore, the degree of flexibility can be easily altered by varying the length along the distal portion which the more flexible portion extends.

The method may further comprise substantially defining said first and second distal portions by an axial line extending from a distal edge of said orthotic towards said heel portion and a transverse line extending transverse to said axial line.

In a preferred embodiment the axial line is located substantially between a first and second metatarsal of said measured foot.

In another preferred embodiment the axial line is located between 10% and 30% across the width of the orthotic from the medial edge.

In a further preferred embodiment the transverse line is located substantially under the first metatarsal base of said measured foot.

The transverse line may be located at around 40% of the length of the orthotic from the distal edge.

The transverse line may be located substantially under the navicular bone of said measured foot.

The transverse line may be located at around 60% of the length of the orthotic from the distal edge.

The transverse line may be located adjacent said heel portion the first and second distal portions therefore extending along the whole length of the distal portion.

The transverse line may be located at around 80% of the length of the orthotic from the distal edge.

In a preferred embodiment the orthotic comprises an upper surface for engaging a foot and a lower surface for engaging an insole of a shoe, wherein said upper surface comprises a substantially continuous surface and the thickness of the first distal portion and the second distal portion are varied by varying the lower surface.

According to another aspect of the present invention there is provided orthotic formed by additive manufacturing and comprising a heel portion for supporting a heel of a person and a distal portion located in front of said heel portion, said distal portion being divided into a first distal portion having a first substantially uniform thickness and a second distal portion having a second substantially uniform thickness thicker than said first thickness.

In a preferred embodiment the first and second distal portions are substantially defined by an axial line extending from a distal edge of said orthotics towards said heel portion and a transverse line extending transverse to said axial line.

In another preferred embodiment the axial line is located substantially between a first and second metatarsal of a foot engaging said orthotic.

In a further preferred embodiment the axial line is located between 10% and 30% across the width of the orthotic from the medial edge.

The transverse line may be located substantially under the first metatarsal base of said foot.

The transverse line may be located at around 40% of the length of the orthotic from the distal edge.

The transverse line may be located substantially under the navicular bone of said foot.

The transverse line may be located at around 60% of the length of the orthotic from the distal edge.

The transverse line may be located adjacent said heel portion the first and second distal portions therefore extending along the whole length of the distal portion.

The transverse line may be located at around 80% of the length of the orthotic from the distal edge.

In a preferred embodiment the orthotic comprises an upper surface for engaging a foot and a lower surface for engaging an insole of a shoe, wherein said upper surface comprises a substantially continuous surface and the thickness of the first distal portion and the second distal portion are varied by varying the lower surface.

According to a further aspect of the present invention there is provided a method of making an orthotic, comprising the steps:— taking measurements relating to a foot or leg residual limb;
creating a digital representation of an orthotic on a display device based on said measurements;
varying the thickness of and/or putting perforations into the digital representation of the orthotic;
using additive manufacturing using a substantially uniform material or materials to create a physical version of the digital representation of the orthotic wherein thicker portions of the orthotic are more rigid and perforated portions of the orthotic are more flexible.

By creating perforations in an orthotic using additive manufacturing, the advantage is provided that the orthotic includes ventilation making it much more comfortable to wear for long periods of time compared to devices of the prior art. Furthermore, the perforations reduce problems where excessive heat and perspiration can cause discomfort, enhance inflammation and encourage the growth of pathogens. It is also the case that by varying the flexibility of the orthotic pathologies of the foot or residual limb or other pathologies can be treated. This can be achieved with great precision.

In a preferred embodiment the perforations comprise a plurality of shapes providing different flexibility.

In another preferred embodiment the thickness of the digital representation of the orthotic is increased in the region adjacent a navicular bone in a measured foot.

In a further preferred embodiment the thickness of the digital representation of the orthotic comprises an increase in the form of a line extending axially along said orthotic substantially parallel to a medial edge of the orthotic.

The thickness of the digital representation of the orthotic may comprise an increase in the form of a line extending from a point under said navicular bone approximately 10 mm in from a medial edge of the orthotic to a point under the heel approximately 10 mm in from the medial edge of the orthotic.

By varying the thickness of the orthotic adjacent the navicular and in particular by doing so using a line, the advantage is provided that a supportive instep in the orthotic is easily created.

According to another aspect of the present invention there is provided an orthotic comprising a body having an upper surface for engagement with a foot or residual limb and a lower surface for engagement with an insole surface of a shoe or prosthetic, the orthotic formed from a material or plurality of materials mixed consistently throughout the structure of the orthotic, the thickness of the orthotic between the upper and lower surfaces and/or the presence of perforations between the upper and lower surfaces varying the flexibility of regions of the orthotic.

The perforations may comprise a plurality of shapes providing different flexibility.

The orthotic may further comprise a substantially inflexible portion having at least one protrusion on said lower surface.

In a preferred embodiment the orthotic comprises a heel reinforcement portion incorporating said substantially inflexible portion and at least one said protrusion.

In another preferred embodiment the protrusion is substantially annular.

In a preferred embodiment the lower surface adjacent said protrusion comprises a substantially planar portion for engagement with the insole surface of the shoe.

In another preferred embodiment the substantially planar portion comprises a plurality of perforations.

According to a further aspect of the present invention there is provided an orthotic for engagement with a foot, the orthotic comprising a body having an upper surface for engagement with a foot and a lower surface for engagement with an insole surface of a shoe, the body including a substantially inflexible portion having at least one protrusion on said lower surface.

By providing a protrusion extending down from the lower surface of an inflexible portion of the orthotic, the advantage is provided that the protrusion creates an indentation into the insole of the shoe in which the orthotic is located and this assists in preventing the orthotic from moving.

In a preferred embodiment the orthotic comprises a heel reinforcement portion incorporating said substantially inflexible portion and at least one said protrusion.

In another preferred embodiment the protrusion is substantially annular.

An annular protrusion is particularly useful as it provides the retaining grip for the orthotic in all directions within the shoe. It is also easy for the protrusion to key into the annular indentation created in the insole as the shoe is put on and taken off the foot.

In a preferred embodiment the lower surface adjacent said protrusion comprises a substantially planar portion for engagement with the insole surface of the shoe.

By having the lower surface adjacent the protrusion as a substantially planar surface the advantage is provided that this limits the extent to which the protrusion can create an indentation into the insole of the shoe. As a result, just sufficient indentation is created without significant damage to the shoe.

In a further preferred embodiment the substantially planar portion comprises a plurality of perforations.

Providing perforations around the rigid portion assists in circulating air around the sole of the foot providing the benefits described above.

The benefits over the state of the art can be summarised as:

The ability to create compliant sections where required without using different materials or by adjusting the thickness of the device. The orthotic developed here is a shell with patterns cut out which is a very thin and compact device. These are both very sought after properties in an orthotic.

The properties of the compliant sections can be controlled very precisely as the design of the pattern takes place in a digital environment and their manufacturing is also digital, so the designed geometry is created with a high level of precision. This level of control over the shape of the patterns is impossible using state of the art manufacturing. Further to this, the compliant sections can be characterised and controlled using finite element analysis and other analytical engineering tools. This is also impossible using traditional manufacturing methods.

The orthotics enable the passage of air by passing through the holes. This is not possible in state of the art Foot Orthotics and a device that enables the passage of air will be more comfortable and aid therapeutic affect where excessive heat and perspiration can cause discomfort, enhance inflammation and encourage the growth of pathogens.

The orthotic weighs less as less material is used. Fewer raw materials are required and less waste is generated.

The patterns can be customised by the patient or clinician enabling more possibilities for personalisation and product differentiation.

Using the methods of the prior art, the stiffness of the Foot Orthotics cannot accurately be varied except by varying the external geometry or adding other materials. These can increase the bulk of the orthotic and complicate the manufacturing process. Using this invention, the properties of the orthotic can be controlled very accurately in different parts of the device while keeping the shell of the orthotic very thin and compact. Compact Foot Orthotics are easier to fit in shoes than bulky ones and are more comfortable in the shoes. Adding external components such as different materials will take time and manual effort adding to the cost of the devices. They can potentially also wear out.

Orthoses of the prior art do not provide ventilation for the foot. Ventilation improves the comfort of the orthoses significantly.

Orthoses with the hole patterns are lighter than prior art devices as they do not use material excessively. Light weight is an asset as it reduces the energy cost of human propulsion.

State of the art orthoses do not provide many opportunities for personalisation of the orthotics.

Foot orthoses that have a combination of materials cannot be cleaned in a domestic washing machine as the original integrity of the device will be damaged. Using the SLS process the materials used can withstand higher temperatures and can be washed or sterilised in an autoclave.

Preferred embodiments of the present invention will now be described, by way of example only, and not in any limitative sense with reference to the accompanying drawings in which:—

FIGS. 16 to 21 are top, bottom, front, rear, right side and left side views of an orthotic of the present invention;

Figure 1:
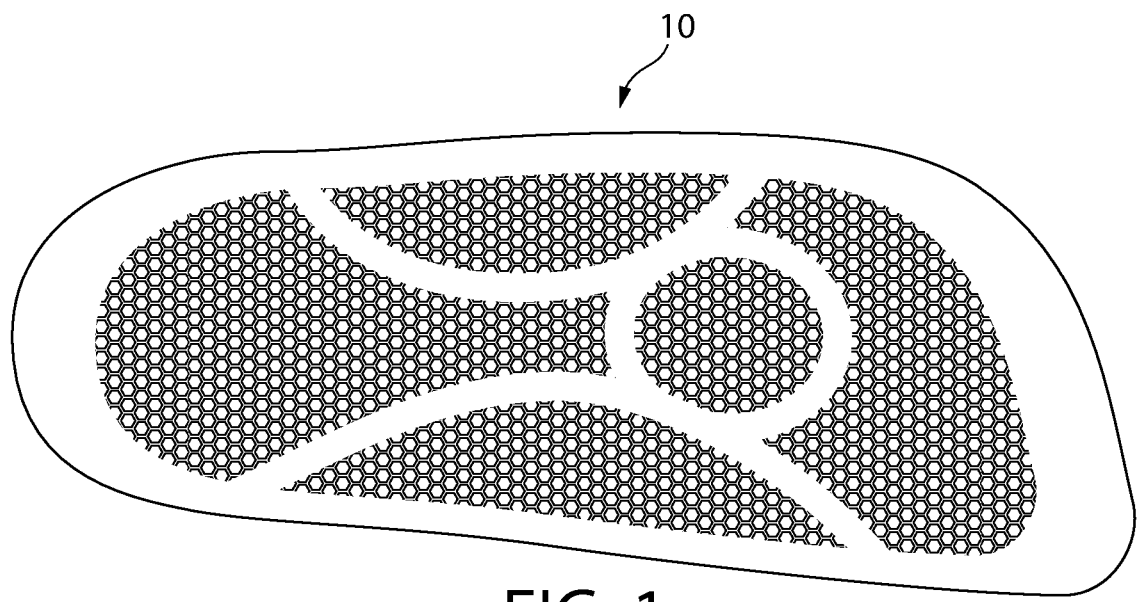
FIGS. 1 and 2 are images of orthotics of the present invention.

Foot orthotics of the present invention are shown in various of the FIGS. 1 to 43 and the different embodiments of the foot orthotic are all indicated by reference numeral 10. The foot orthotic 10 is created by taking measurements from a patient's foot or from a residual limb part of a patient's leg. For the purposes of this description the embodiments shown in the figures relate to an orthotic for engagement with a patient's foot. Techniques for taking such measurements are familiar to person skilled in the art and include direct capture using a digital 3-D scanner or in direct capture where an impression of the foot is obtained using a plaster cast or foam box which is in turn digitised using a 3-D scanner. That measured data is then used to create digital representation of an orthotic which is displayed on a display device, for example a computer screen, using CAD software. The initial basis for the digital representation of an orthotic is to create a digital representation of such a device which, were it created and placed against the measured foot, would engage the vast majority of the sole of the foot and would have a consistent thickness of, for example, 3 mm. Examples of such a digital representation of an orthotic are indicated at 12 in FIGS. 3 to 5.

This basic representation of an orthotic can be divided into a heel portion 14 and a distal portion 16 which is located in front of the heel portion in the direction of the toes of the foot. The distal portion 16 is then also divided into two portions, a first distal portion 18 and a second distal portion 20. In the example shown in FIG. 25, the first and second distal portions are separated by an axial line 22 which extends from a distal edge 24 of the orthotic 10 in a direction towards the heel portion 14 and running substantially parallel to the medial edge 26. The positioning of the axial line 22 is typically between the first and second metatarsals which is generally between 10% and 30% of the width across the orthotic from the medial edge 26 to the lateral edge 27.

The boundary between the first distal portion 18 and the second distal portion 20 may be further defined by a transverse line which extends transverse, or even perpendicular to the axial line 22. In the example shown in FIG. 5 three examples of transverse line is are indicated at 28, 30 and 32. These lines are located at 40%, 60% and 80% respectively of the length of the orthotic 10 as measured from the distal edge 24 and would sit approximately under the base or proximal end of the first metatarsal, the navicular and extending all the way to the heel portion. In the examples shown in FIGS. 22 to 27 the first portion extends all the way back along the orthotic to the heel portion 14. If the transverse line 28, at 40% of the length of the orthotic and under the metatarsal base, is being used to define the first distal portion, the first distal portion is defined by the axial line 22 as it extends from the distal end 24 back to the transverse line 28 and then by the extending from the axial line 22 to the medial edge 26. It is therefore this distal and medial quadrant which forms the first distal portion with the second distal portion being the remainder of the distal portion 16. The same principle applies if the transverse line is the transverse line 30 at 40% and under the navicular. The transverse line 32, at 80% of the length of the orthotic, crosses the heel portion and therefore it is not necessary to define a separate quadrant within the distal portion 16 and the first distal portion 18 extends along the whole length of the distal portion 16.

Once the first and second distal portions 18 and 20 have been defined the thickness of the digital representation of the orthotic can be reduced in one of the first and second distal portions. An orthotic made according to the digital representation will then have a thinner portion and a thicker portion with the thinner portion being more flexible. In the interests of comfort, it is preferable that the upper surface of the orthotic 10, which is engaged with the foot, is formed as a substantially continuous surface and therefore the thinning of the first distal portion is created by a step along the axial line 22 and also along the transverse line (if necessary, that is if the transverse line is 28 or 30 are being used to define the first distal portion 18, a step on the transverse line is not formed if the transverse line is line 32 since this is substantially within the heel portion).

In the above-described embodiments the material is therefore reduced from under the first metatarsal. With the transverse line 28 at 40% this encourages first metatarsal progressive flexion. With the transverse line 30 at 60% this encourages full arch progressive flexion and with the transverse line 32 at 80% this encourages pronation motion flexion.

Alternative to the thinning portion being the distal medial quadrant, the lateral medial quadrant could be thinner to be more flexible. This will encourage supination motion flexion.

Additional rounding and smoothing of the digital representation of the orthotic may be applied and perforations 34 created in the digital representation 12 of the orthotic. Where the first distal portion 18 of the orthotic 10 is thinner than the second distal portion 20 it may not be possible to include perforations if this will make the orthotic unable to support the weight of the person standing on it.

Once the design of the orthotic has been completed in the manner described above the data relating to that image can be exported and an orthotic created using additive manufacturing.

Figure 28:
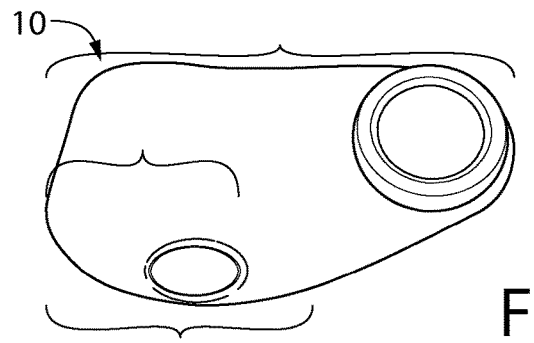
FIGS. 28 to 39 are representations showing the steps in the design process of an orthotic of the present invention.
Figure 29:
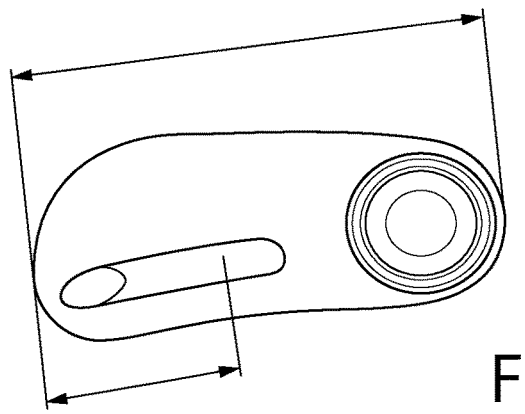
Figure 30:
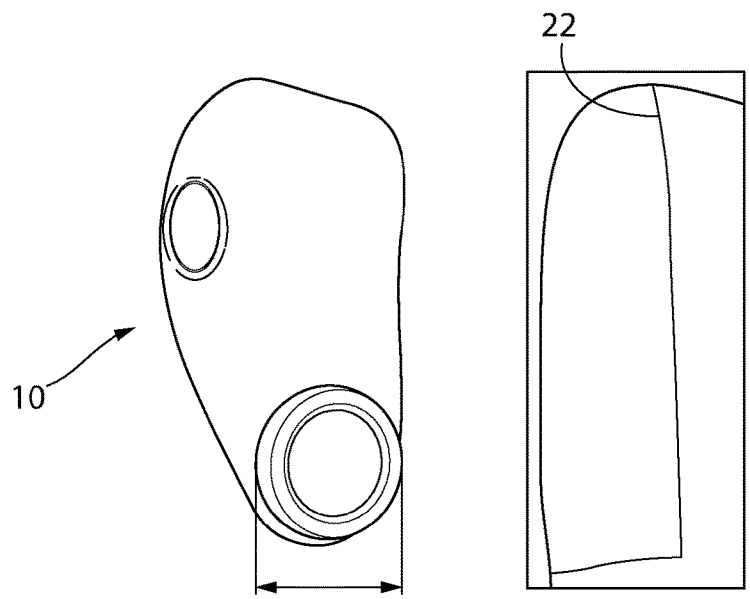

The design process is further explained in FIGS. 28 to 39 as follows. Referring to FIG. 28 the full length of the orthotic 10 is measured and the 40% or 60% length, as required, is measured and marked from the distal end 24 of the orthotic. The width of the orthotic is also measured. Referring to FIG. 29, the orthotic in question as a total length of 185 mm and a first metatarsal progressive flexion is required resulting in the marking of a line at 40% this being at approximately, and as close as the software will allow, to 75 mm. Referring to FIG. 30, the axial line 22, between the first and second metatarsals is identified from the scan of the foot or foam box and marked on the digital representation of the basic orthotic.

Figure 31:
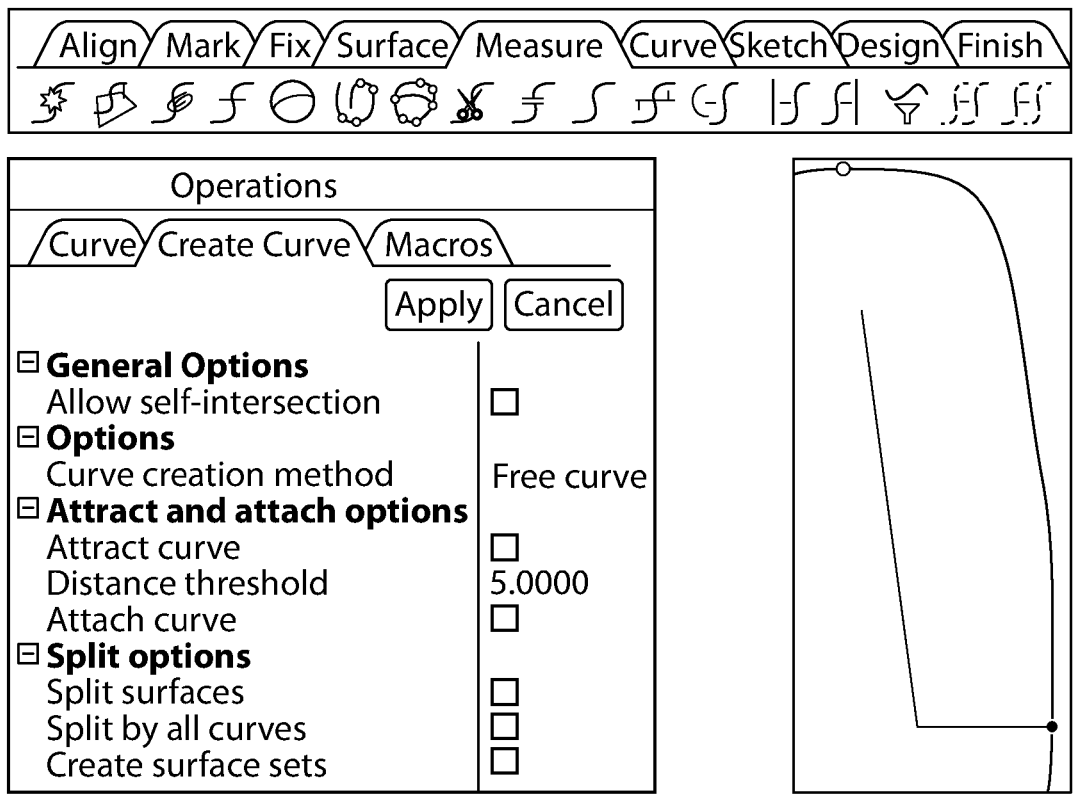
Figure 32:
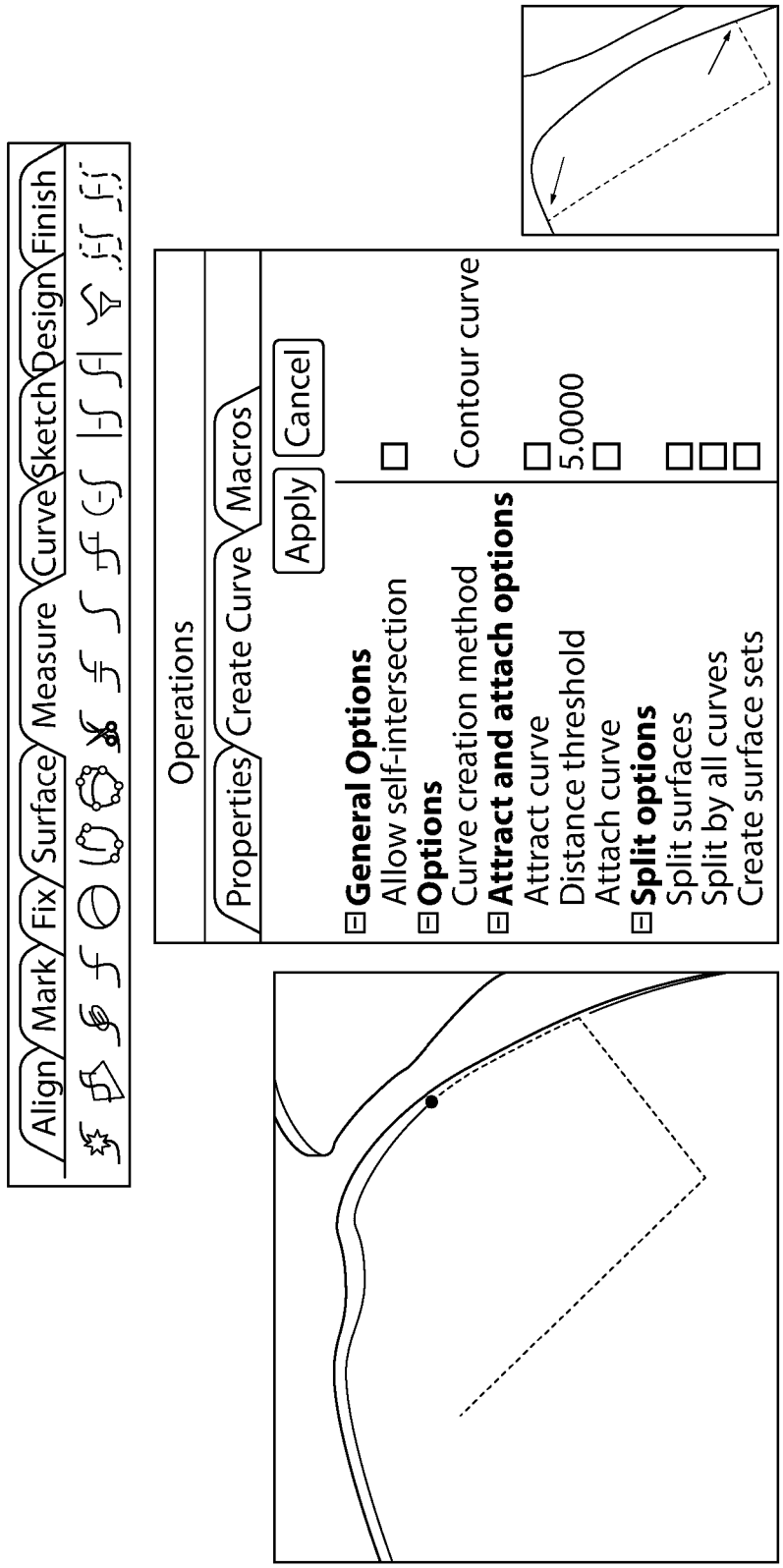
Figure 33:
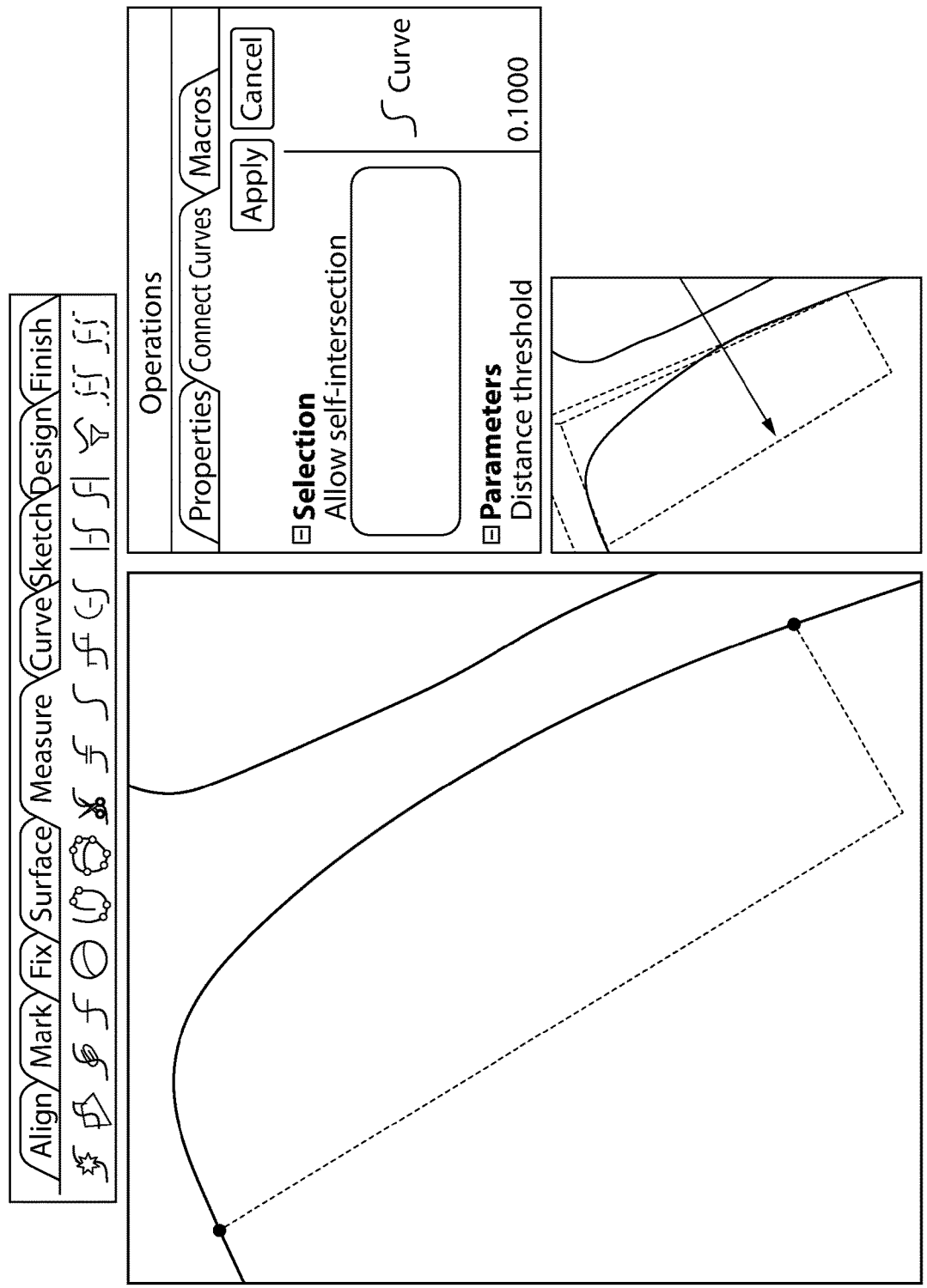
Figure 34:
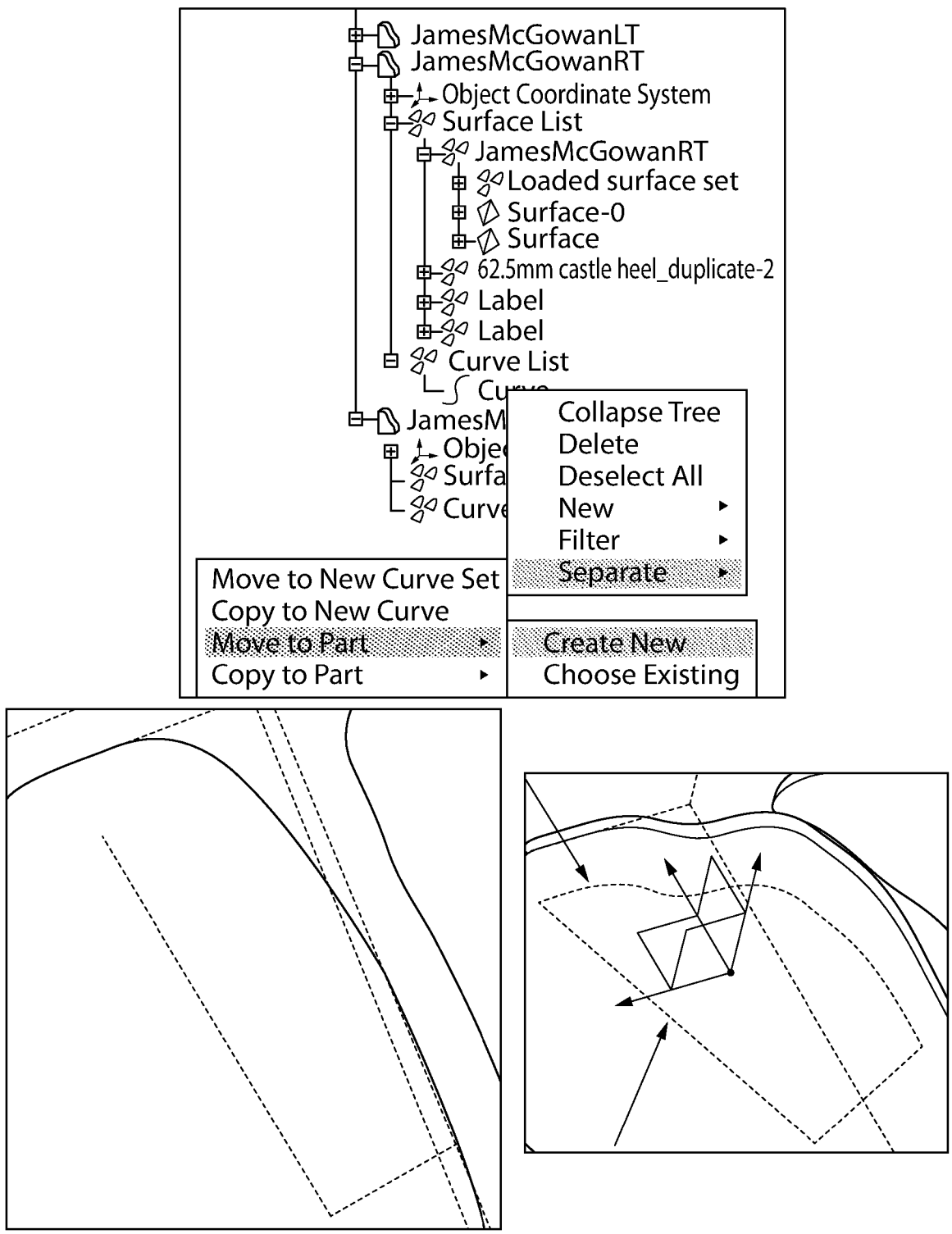
Figure 35:
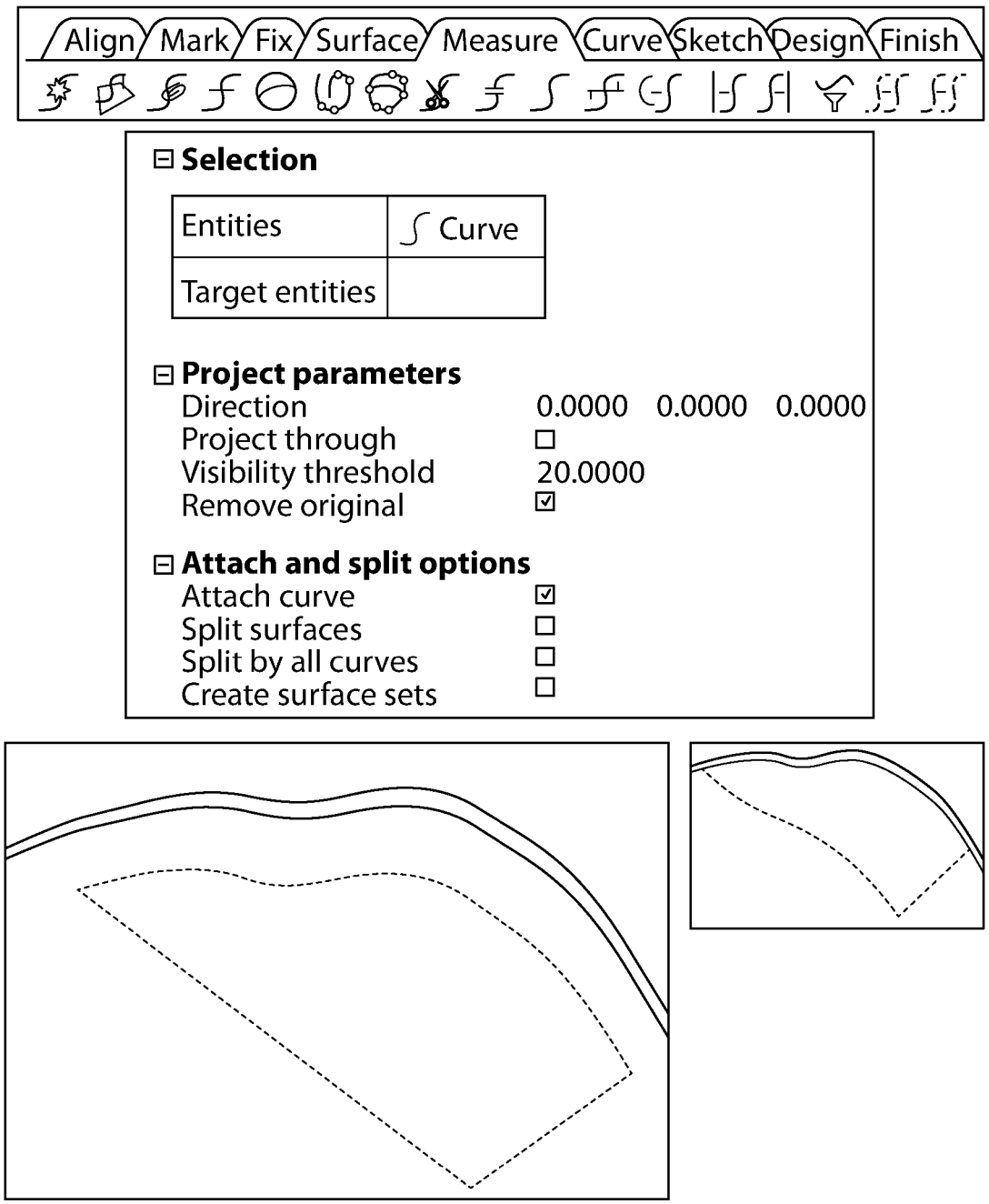
Figure 36:
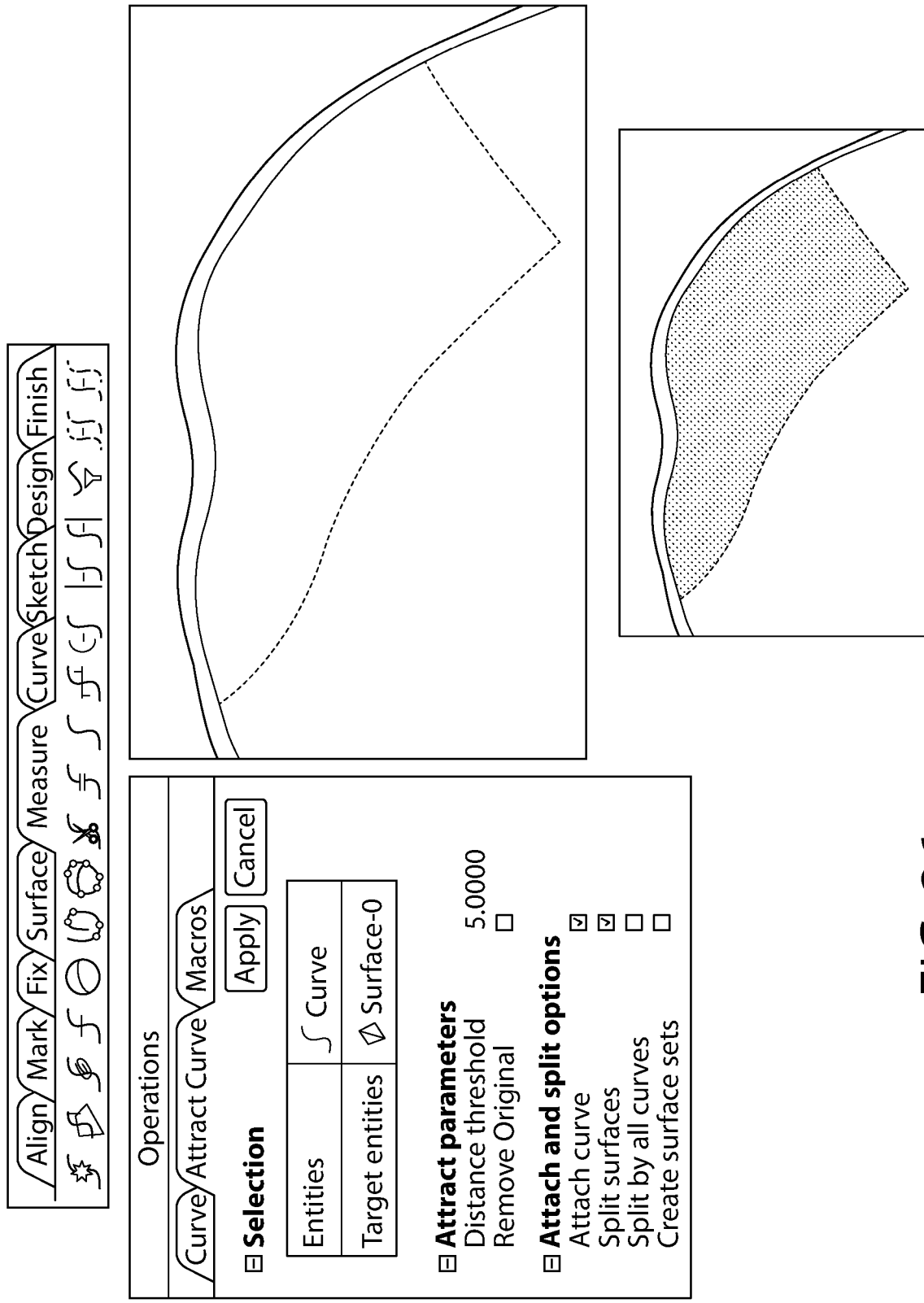
Figure 37:
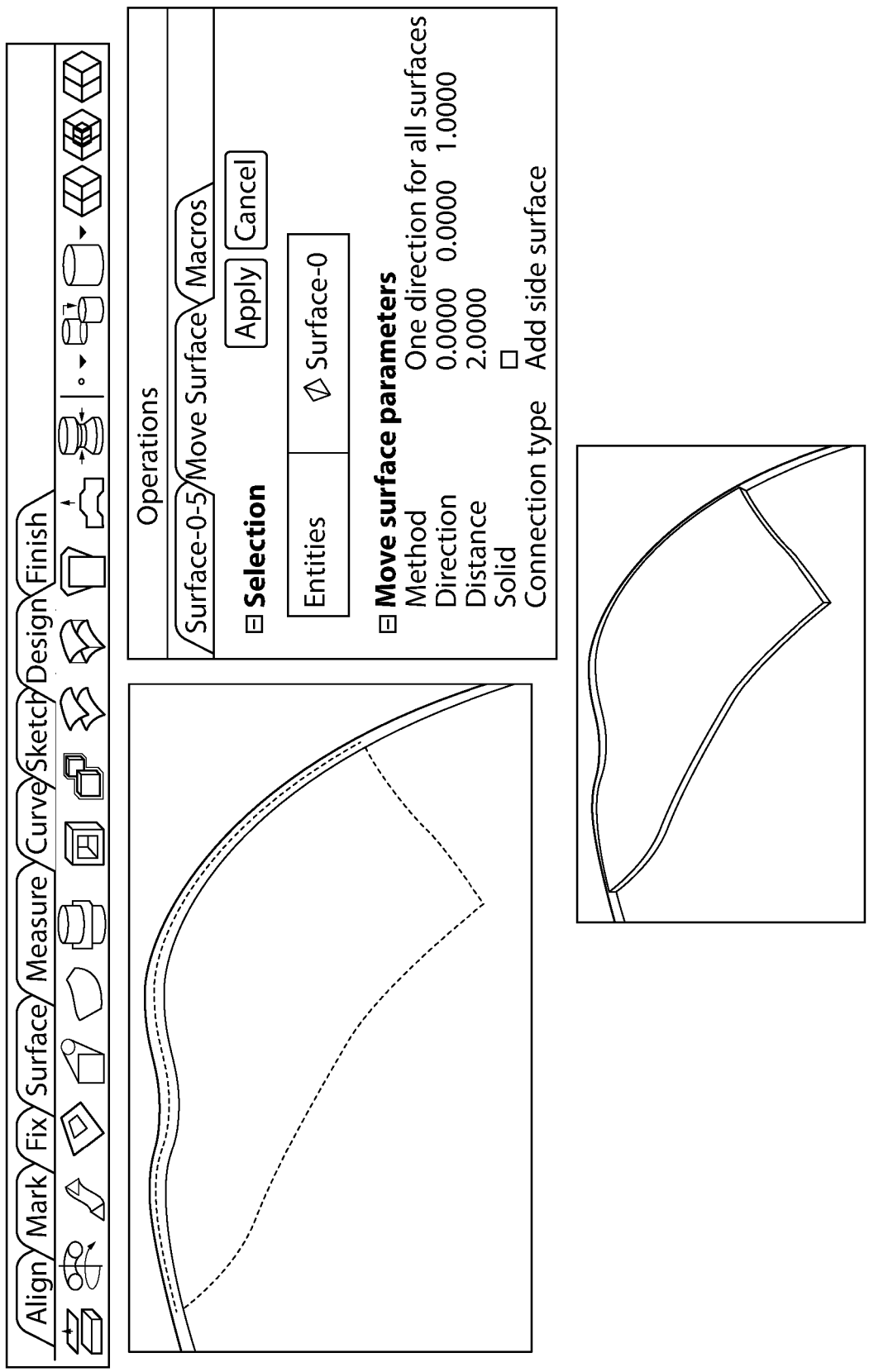
Figure 38:
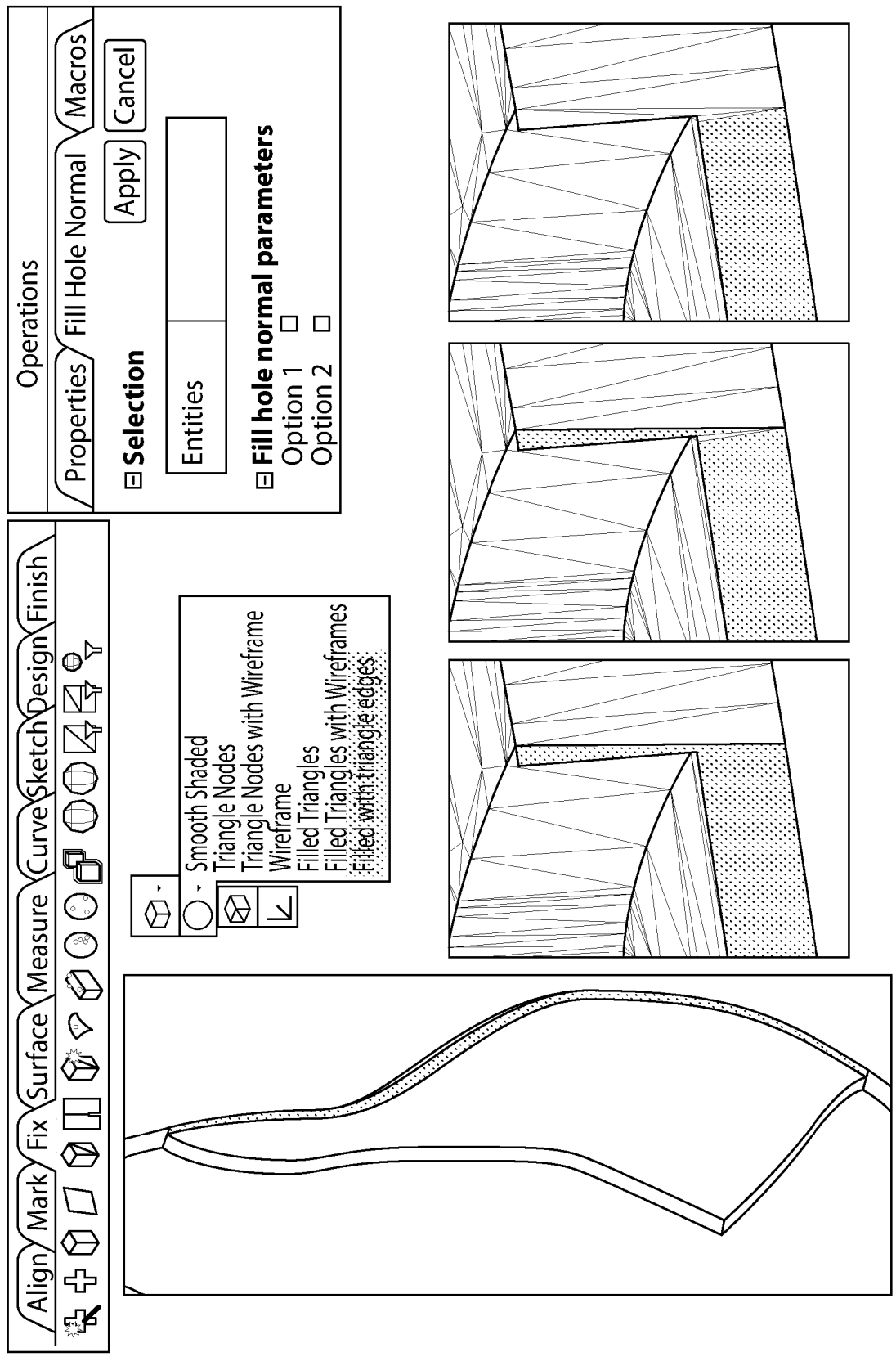
Figure 39:
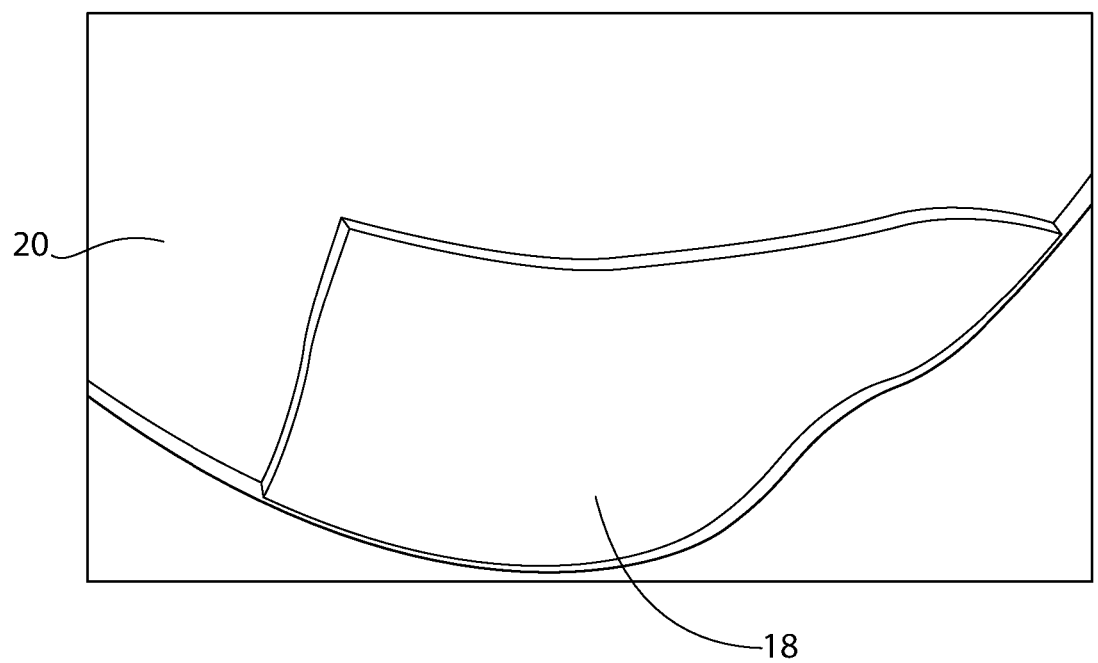
Figure 40:
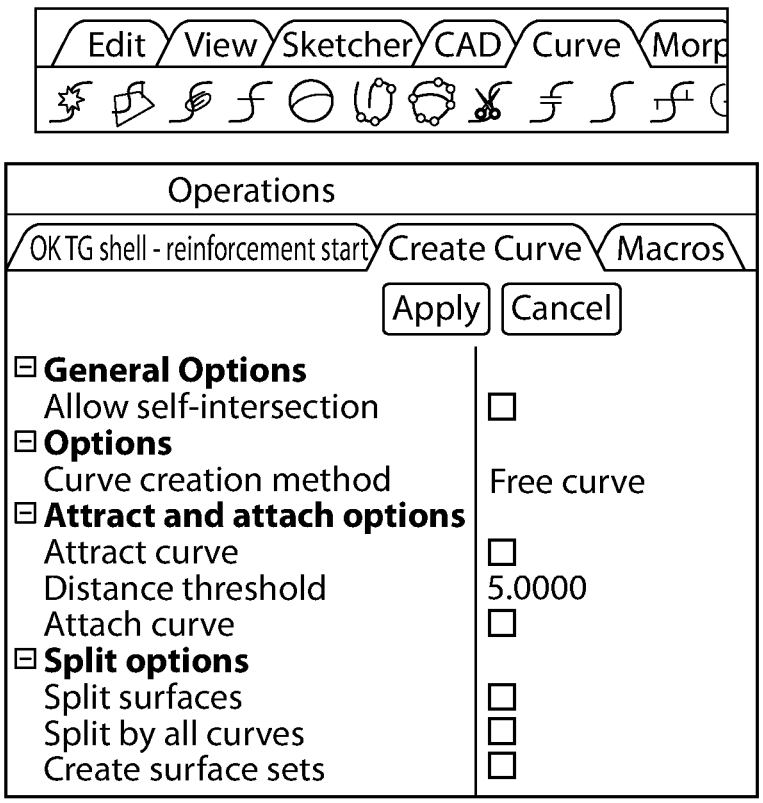
FIGS. 40 to 43 are representations showing the steps in the design process of another orthotic of the present invention
Figure 40:
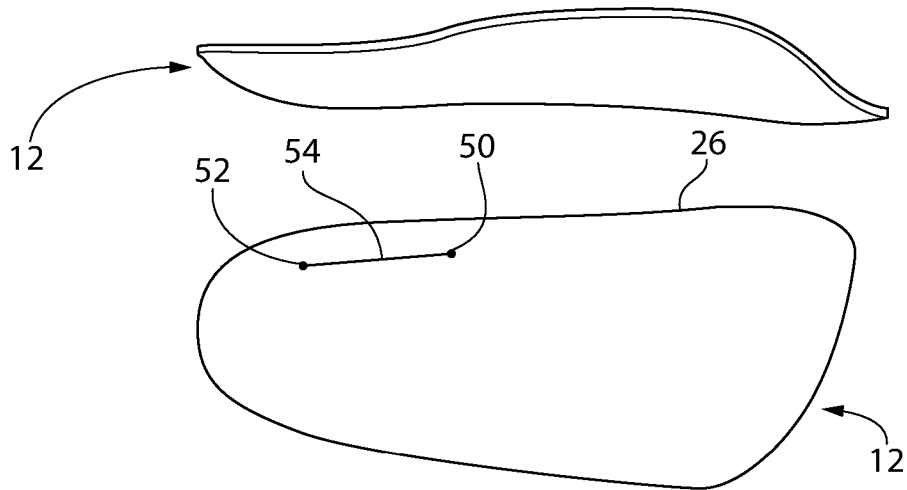

FIGS. 31 to 37 step through the process of using lines to define the first distal portion with the drawing of lines shown in FIGS. 31 and 32, the curved lines being connected to define the first distal portion in FIG. 33, the curve being moved and projected in FIGS. 34 and 35 and the surface being moved (thereby thinning the material) in FIGS. 36 and 37. It should be noted that the material should not be thinner than sufficient to support the weight of the person using the orthotic. For example 1 mm for patients less than 60 kg and 1.5 mm for patients greater 60 kg. Any holes or errors are corrected and smoothed in FIG. 38 before the first distal portion is fully defined and shown in FIG. 39.

Figure 12:
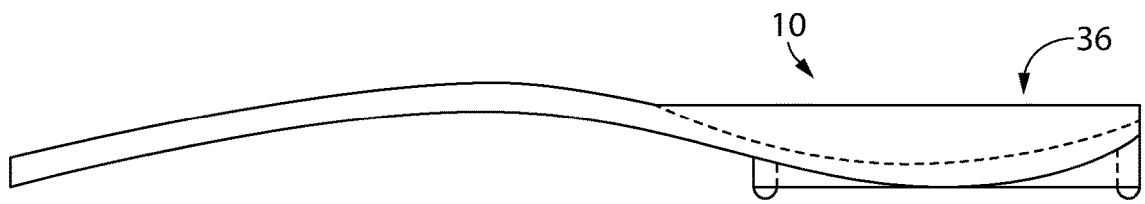
FIGS. 12 to 15 are side, perspective, partial and line rendered views of an orthotic of the present invention.
Figure 13:
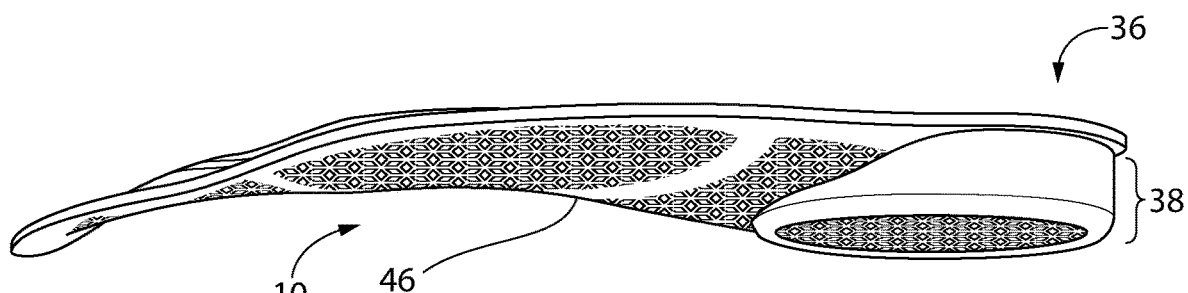
Figure 14:
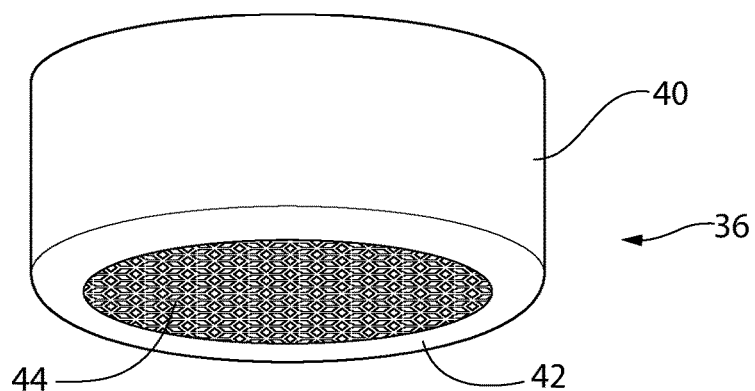
Figure 15:
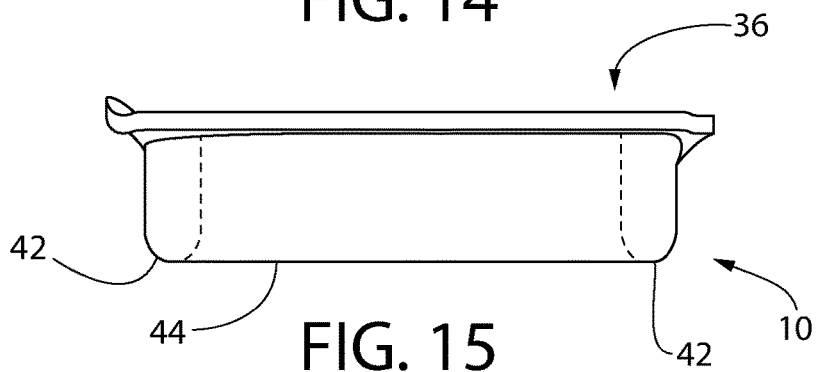
Figure 22:
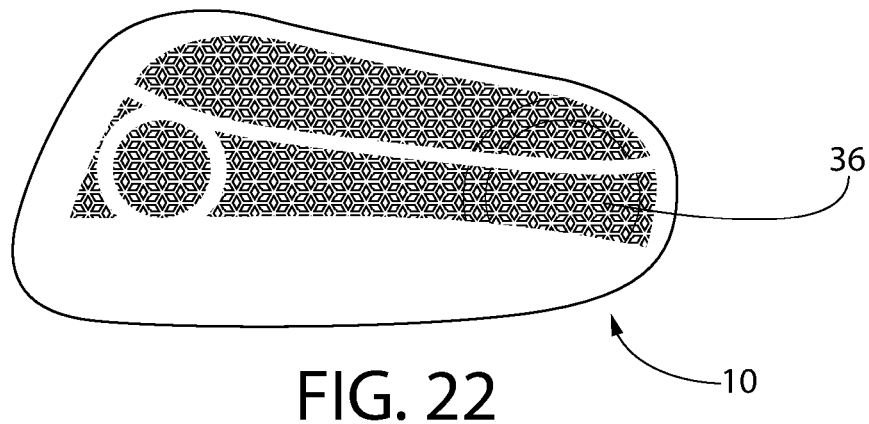
FIGS. 22 to 27 are top, bottom and end views, a line view from above showing detail of the underside, a side and a perspective view from underneath of an orthotic of the present invention.
Figure 23:
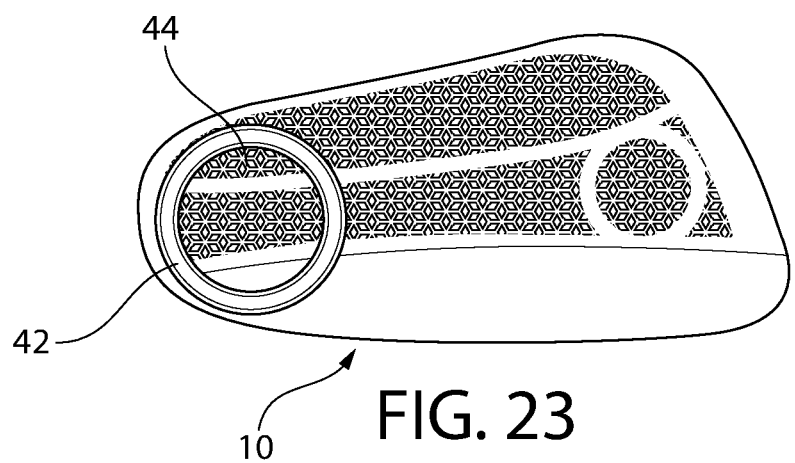
Figure 24:
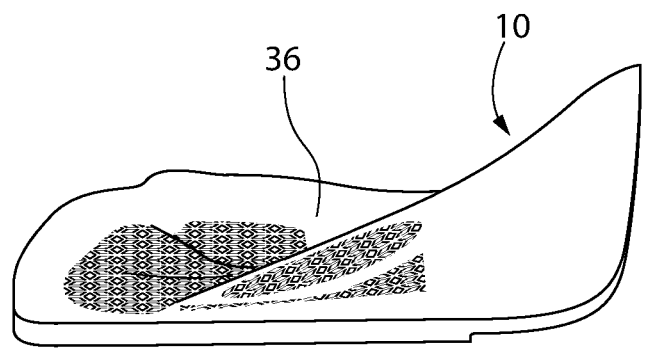
Figure 25:
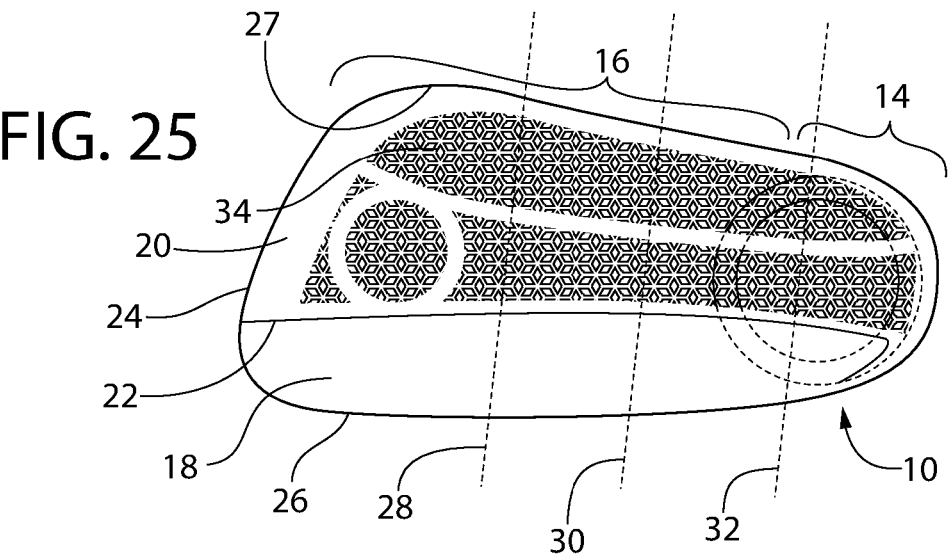
Figure 26:
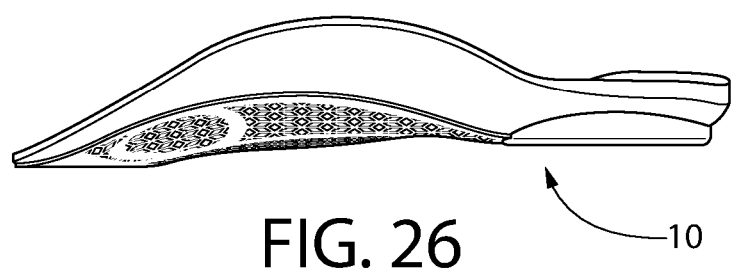
Figure 27:
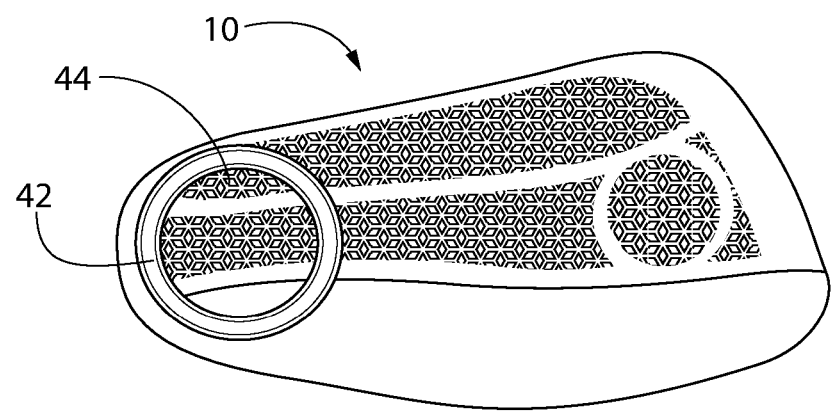

The shape of the heel portion 14 will now be described with reference to FIGS. 9 to 27 and particular reference to FIGS. 12 and 15. The heel portion 14 is substantially rigid and is thicker than the distal portion 16. The heel portion 14 has an upper surface 36 which engages the heel of a foot and is shaped according to the measurements taken of the foot or from the foam box. Alternatively the heel may be a standard shape which fits the majority of heel shapes. A lower portion 38 of the heel portion 14 is shown as though separated from the orthotic in FIG. 14. This lower portion 38 is annular and has an annular outer wall 40. This lower portion 38 has a protrusion extending from the annular wall 40 thereby forming an annular ridge 42. Immediately adjacent the annular protrusion 42 is a bottom surface 44 of the lower portion 38. This bottom surface 44 does not extend as far down as the annular protrusion 42. Apertures, of the same type as aperture is 34 extend from the bottom surface 44 to the upper surface 36 providing ventilation and reducing the weight of the orthotic. The annular protrusion 42 is typically 1 mm to 2 mm beyond the bottom surface 44. As a result, when the orthotic 10 is placed in a shoe the weight of a person pushes the annular protrusion 42 into the insole of the shoe causing an indentation. This indentation locates the orthotic in the correct position and with the protrusion 42 sitting in the indentation the orthotic 10 does not move within the shoe. 1 mm to 2 mm is sufficient to locate and retain the orthotic in position but not sufficient to significantly damage the insole of the shoe. Once the protrusion 42 has sunk into the insole to its full depth the adjacent bottom surface 44 stops any further indentation occurring.

The method of the present invention may be used to form an orthotic with an arch reinforcement. This process will be described with reference to FIGS. 3 to 8 and FIGS. 41 to 44. The start of this process is the same as described above where the foot is measured (either directly or indirectly) and a digital representation of an orthotic is created. The arch reinforcement is in the form of a thickened ridge extending along a portion of the orthotic which significantly increases the stiffness, even to the point of complete inflexibility, of the orthotic.

Figure 41:
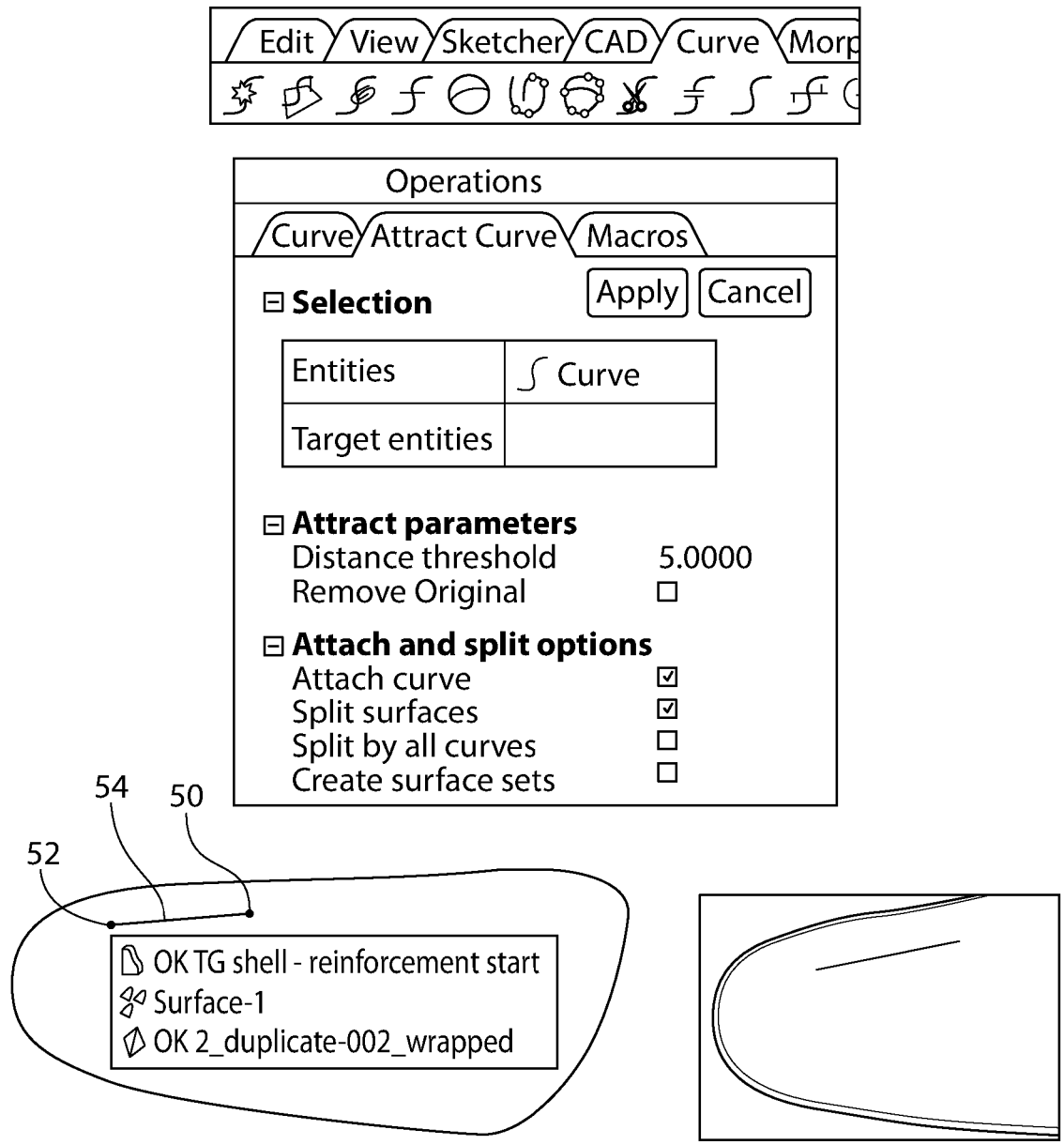
Figure 42:
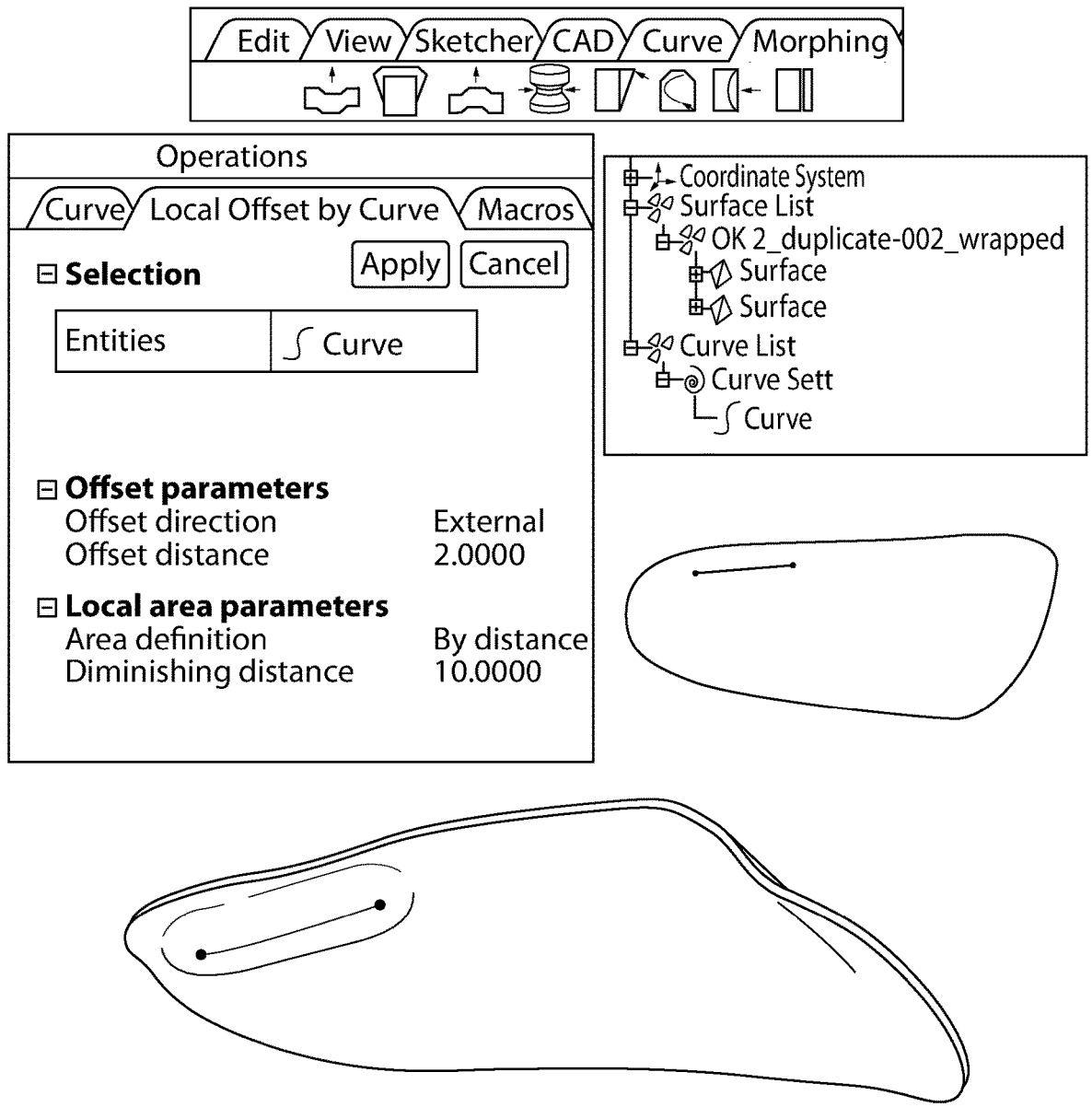
Figure 43:
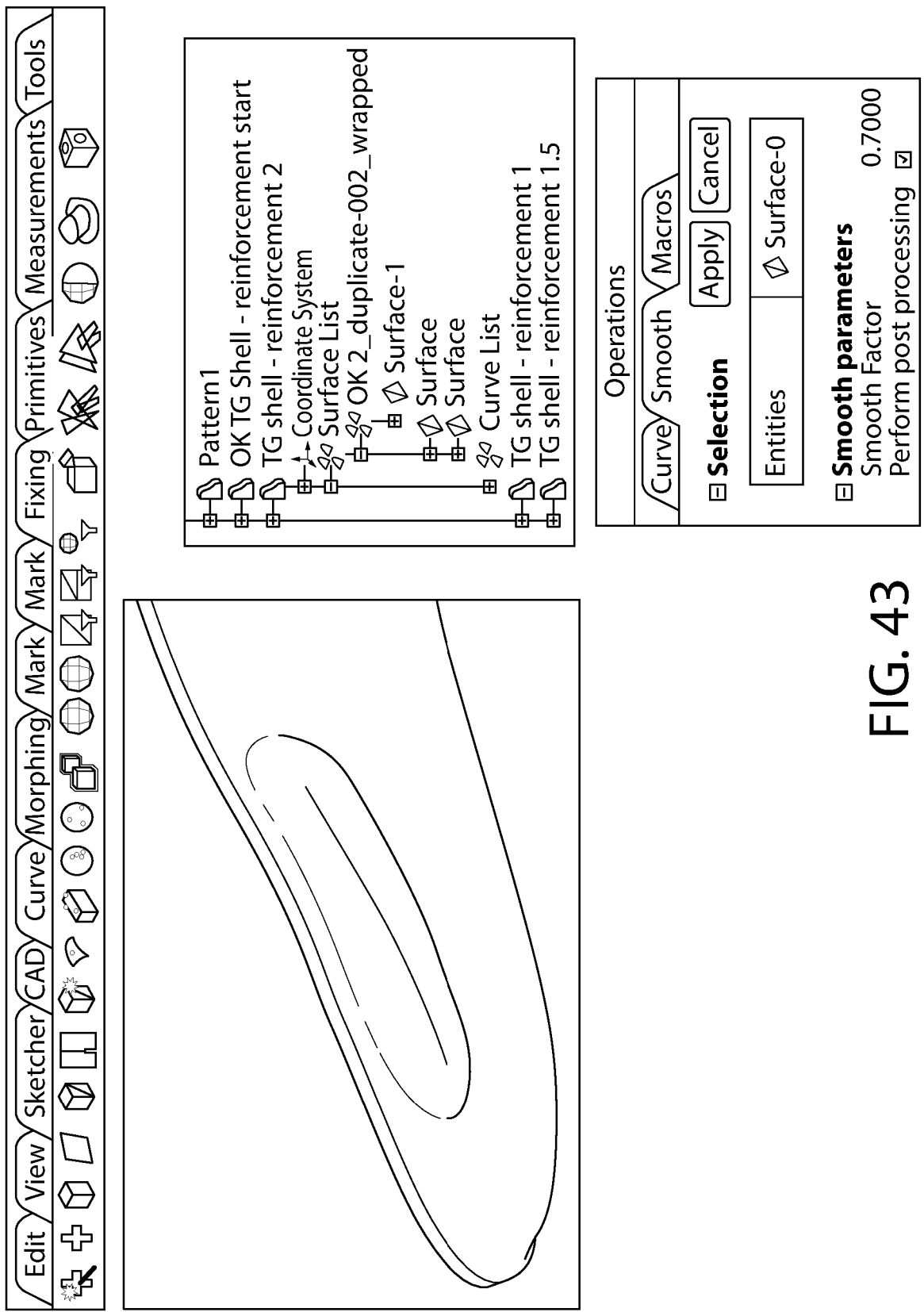
Figure 44:
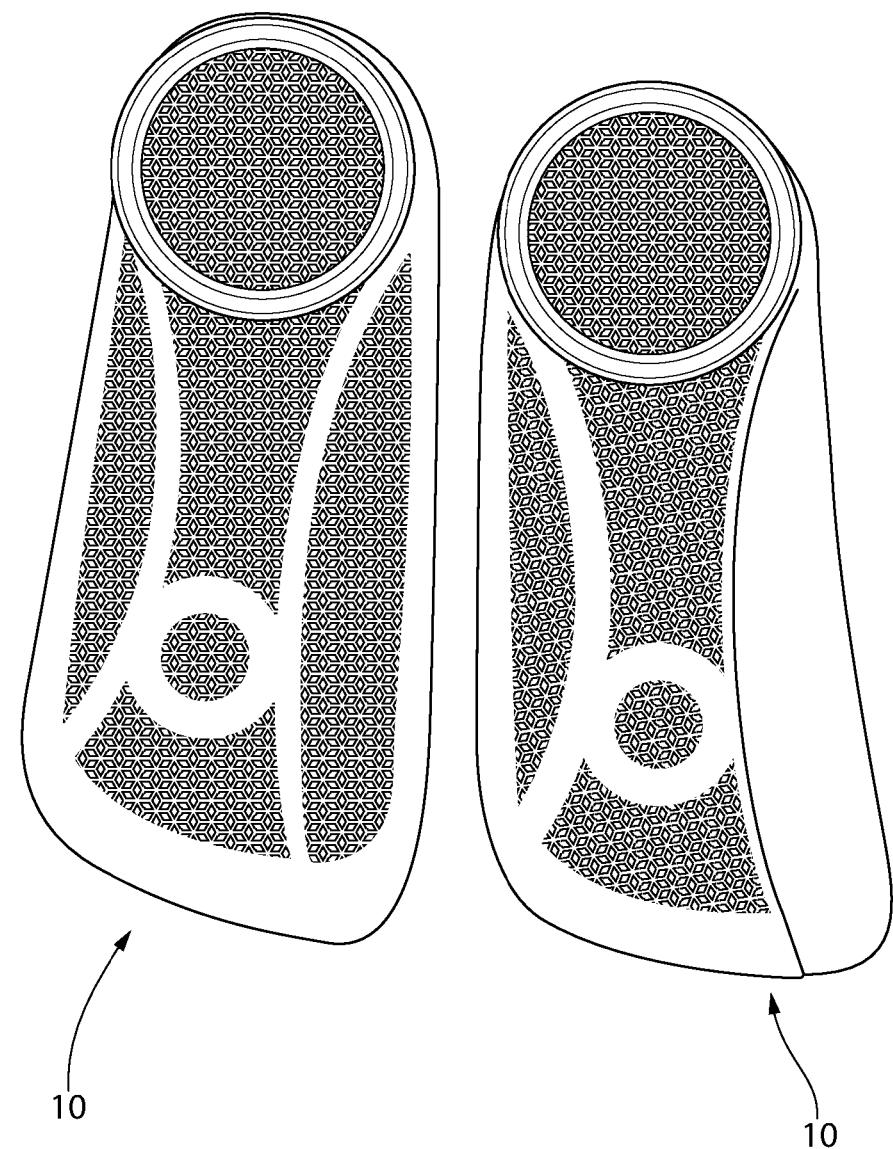
FIG. 44 is an image of two further embodiments of the present invention.
Figure 46:
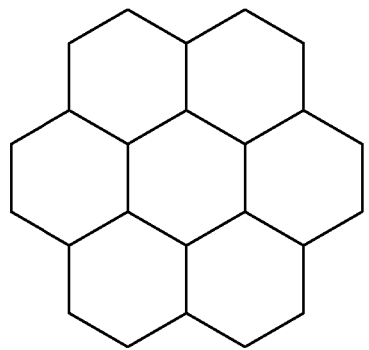
FIGS. 45 to 48 are schematic representations of the perforations used in embodiments of the present invention.
Figure 48:
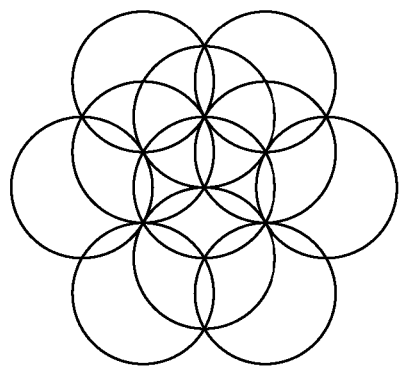
Figure 45:
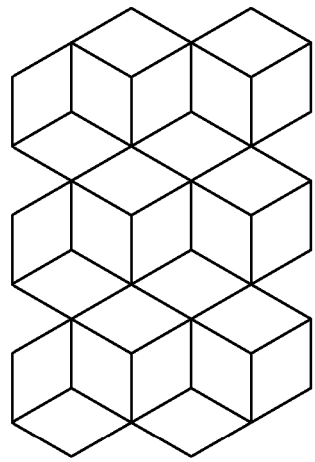
Figure 47:
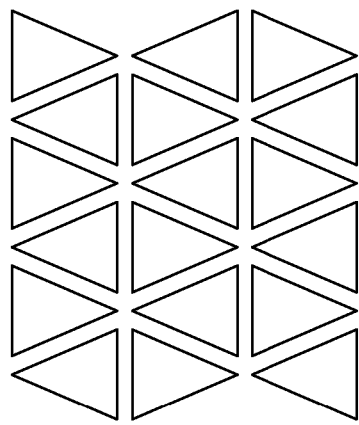

FIGS. 40 to 43 step through the process of creating the arch reinforcement. A first point 50 is identified and this is located below the navicular bone approximately 10 mm in from the medial edge 26. A second point 52 is also identified and located approximately 10 mm in from the medial edge and behind the first point 50 approximately below the centre of the heel. This is the line identified by reference numeral 54 that is the basis for the thickened arch reinforcement. As shown in FIG. 41, these points 50 and 52 are connected by a line, drawn as a free curve to follow the contour of the surface of the orthotic. In FIG. 42 it is shown how the line 54 is converted into a ridge using a "local offset by curve" having a thickness of around 10 mm which is then smoothed and finished as shown in FIG. 43. Perforations can be added and can extend through the whole depth of the ridge thickening as particularly shown in FIGS. 9 to 11. FIG. 8 shows examples of cross sections through the arch reinforcement and the embodiment described above is shown schematically in the drawing A of FIG. 8. Alternative arch reinforcement profiles are shown in drawings B, C, D and E.

Once this process of design is complete the digital representation 12 of the orthotic can be converted into the orthotic 10 using additive manufacturing techniques and apparatus.

The following additional description is provided in order to assist in the understanding of the present invention.

The process described below provides a way to create rigid and compliant sections to a Foot Orthotic or to any other orthotic or prosthetic device without adjusting the outer shape of the device. This way, the orthotic can be made very thin and compact. As the orthoses are bespoke, their shape is different every time and the precise geometry of the pattern is different every time.

The process includes applying a series of patterns that are cut through the shell that is the Foot Orthotic device. These patterns can vary in terms of geometry, how much material is removed (how thick the "holes" are) and where they are placed. The compliance/stiffness of the Foot Orthotic can be varied by placing patterns that cut out more material to compliant sections. Typically the perforations are hexagonal or rectangular but can also be triangular, round, pentagonal or any geometric shape determined useful. Typically there is at least 0.5 mm material between each hole in the structure.

Furthermore, supporting solid line structures can be added where necessary. The basic solid structure around the edge follows the contour of the Foot Orthotic and is offset inside it 1-10 mm. The additional reinforcement pattern is scaled to fit to size from a general template and the thickness of the lines can be between 2-20 mm. The template pattern can be also elongated or widened to fit the individual insole shape. Examples of these Foot Orthotic devices are shown in FIGS. 1 and 2 and FIGS. 16 to 21.

The design and manufacturing process can be described in summary as follows:

1. Capture the geometry of the foot or other body part in question
2. Design the orthotic/prosthetic device as it is known to a person skilled in the art with a CAD system. This will create a shell where the perforations will be added. The thickness of the shell may vary.
3. Add perforations and the supporting lines along with any other additional features to the shell.
4. Manufacture the file directly from the CAD file via Additive Manufacturing (AM), also known as 3D printing.

Figure 2:
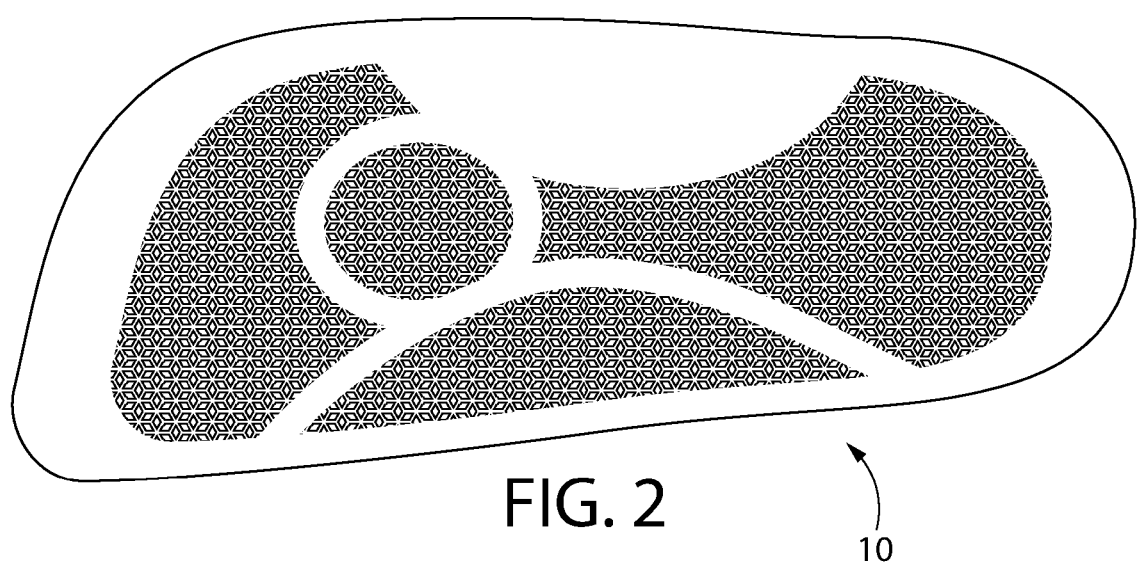

One example could be having a semi rigid shell where the heel and/or the arch of the foot are left "solid" and the rest of the Foot Orthotic is cut with a pattern to keep the functional parts of the Foot Orthotic rigid and removing material where it is not needed. The patient or clinician can also customise their orthotic by selecting different patterns that have similar compliance. For example, the shape of the perforations shown in FIGS. 1 and 2 are different which lead to different degrees of flexibility. Furthermore, a portion of the orthotic shown in FIG. 2 remains solid and contains no perforations compared to that shown in FIG. 1.

These kinds of structures are impossible to create using traditional orthotics manufacturing methods which include vacuum forming thermoplastic materials such as polypropylene on a plaster positive or milling EVA foam or polypropylene. However, additive manufacturing methods, such as selective laser sintering (SLS) allow these complex shapes to be created automatically from CAD files. Additive methods are the only manufacturing methods how these complex patterned orthotics can be created.

A method of making an orthotic according to the present invention will now be described. The process begins when the patient gets sent to an orthotic/podiatric consultation. This consists of a clinical assessment of the patient's condition and from that assessment a description or order of the Foot Orthotic needed to correct the clinical problem. In this stage the patient foot shape has to be captured. This can be taken using plaster cast, foam boxes or in rare occasions via digital 3D scanners.

In a prior art manufacturing process the cast or foam box is scanned in a digital 3D scanner to get a digital impression of the foot in question. The orthotic design then takes place in a dedicated computer assisted design (CAD) system. This design process consists of cleaning up the scanned surface, manipulating the foot shape to achieve the required corrections to the foot to fix the biomechanical anomalies in the foot, adding intrinsic and/or extrinsic posting, pads or bars.

Figure 3:
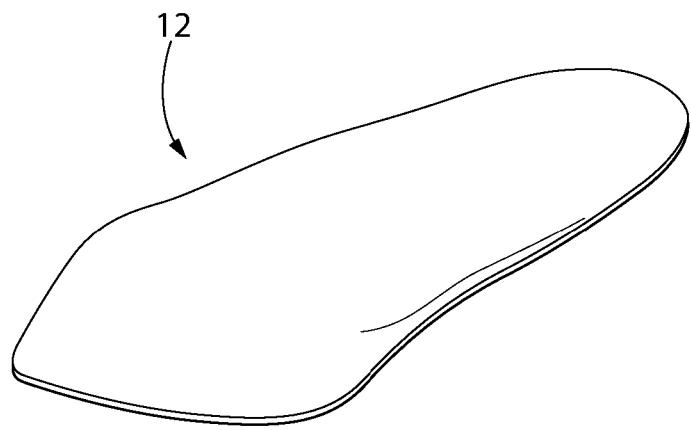
FIGS. 3 to 7 are digital representations of an orthotic demonstrating steps used in the present invention.

The corrected geometry can then be further manipulated digitally. In this invention, the top surface of the Foot Orthotic will be exported to another, more sophisticated CAD software. All the orthotic interventions and manipulations etc. are in this geometry. FIG. 3 shows the top surface of a foot orthotic in the middle of the CAD process.

Figure 4:
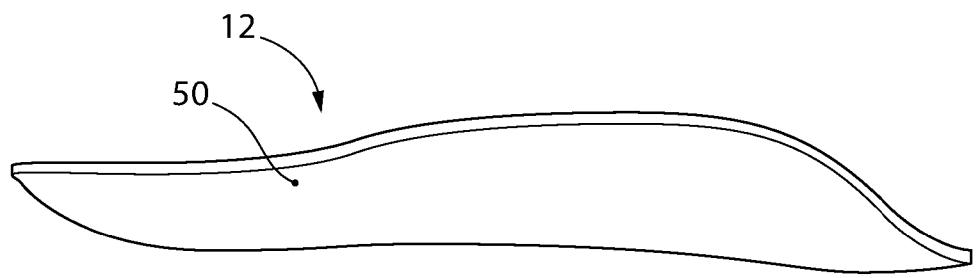
Figure 5:
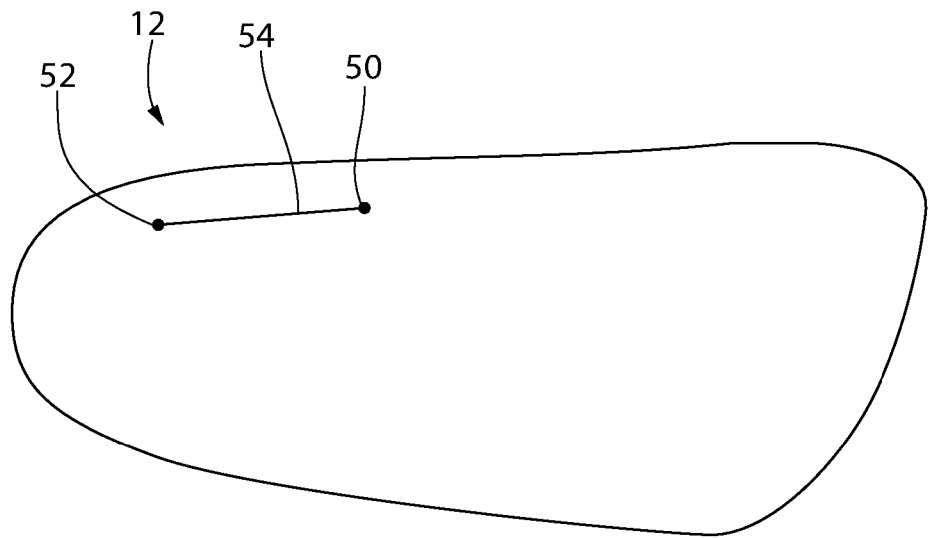

This shell is first turned into a solid object by giving it a constant thickness. Then, further design can take place. An example of a solid Foot Orthotic shell produced using CAD software is shown in FIG. 4.

If the purpose of the Foot Orthotic is to provide arch reinforcement, the design process continues as follows. The work begins from the shell as explained before the perforations are added. The design objective is to thicken a specific region of the shell to give it more rigidity to achieve a biomechanical intervention.

This thicker region is initially defined by a line. The first point, indicated at 50 on FIG. 4, should be under the navicular, or under the highest point of the arch, as required by the anatomy and the desired clinical intervention. This point is not placed on the edge of the Foot Orthotic but approximately 10 mm "inside" from the edge.

The second point 21 should be almost straight behind the first one when going parallel to the edge of the Foot Orthotic and staying about 10 mm "inside" from the edge of the Foot Orthotic. The length of the line is usually 30-50 mm but can be more or less depending on the bespoke shape and functional requirements. Connecting the points 50, 52 a line 54 can be drawn, as seen on FIG. 5.

Figure 6:
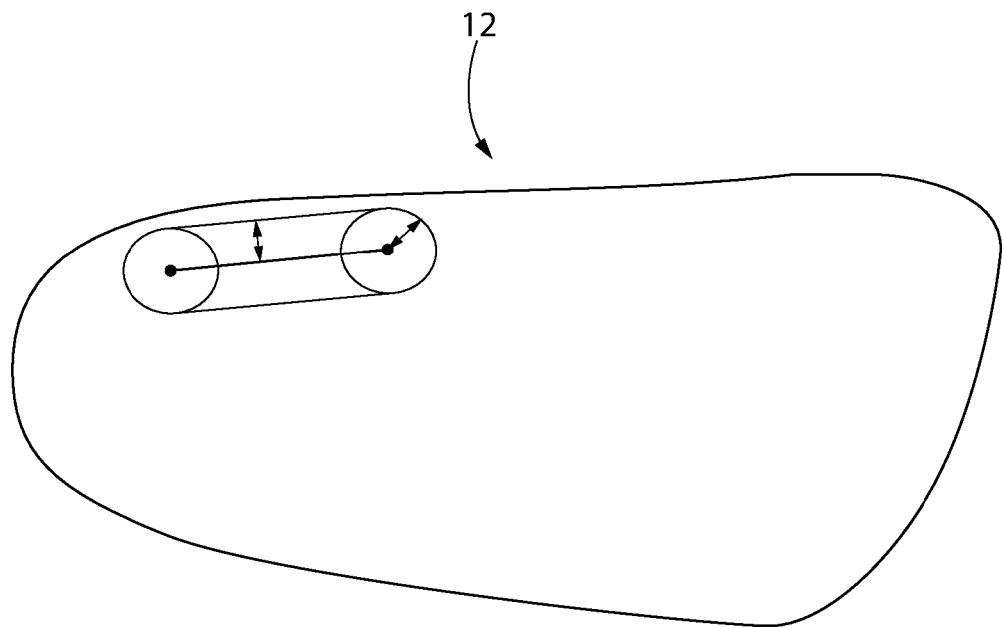
Figure 7:
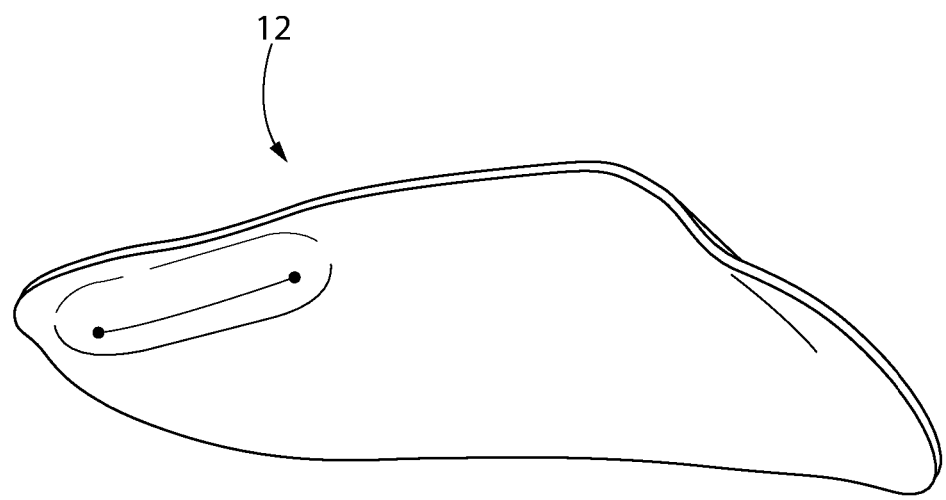
Figure 8A:
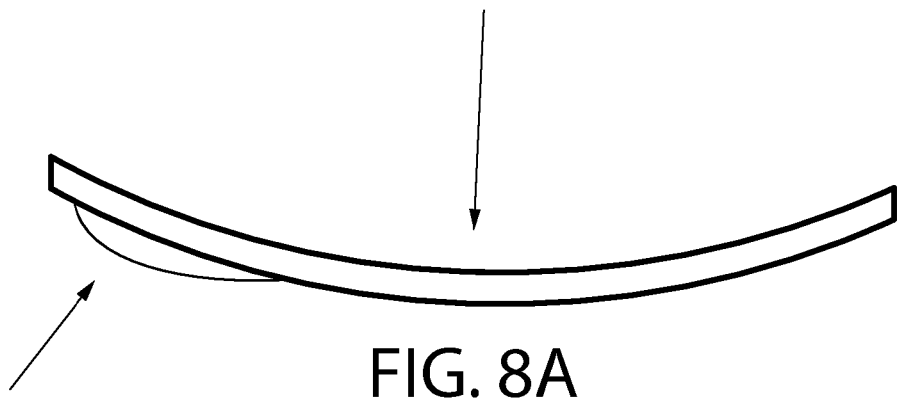
FIG. 8 is a schematic representation of a portion of an orthotic.
Figure 8B:
Figure 8C:
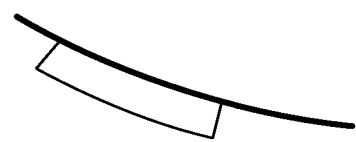
Figure 8D:
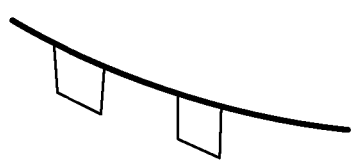
Figure 8E:
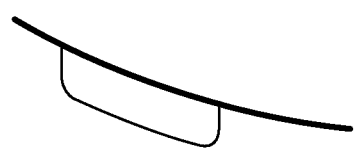
Figure 9:
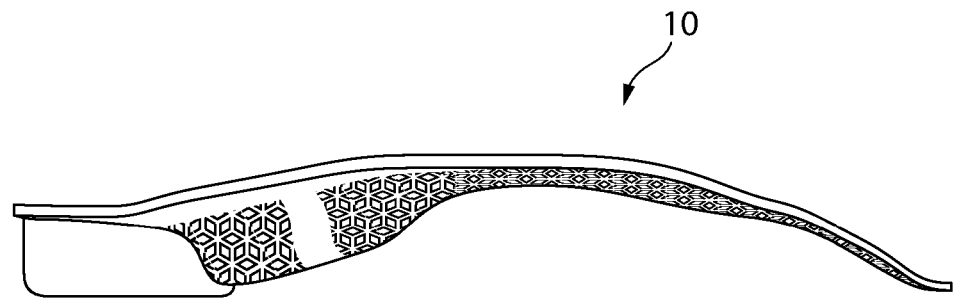
FIGS. 9, 10 and 11 are sectional views of an orthotic of the present invention.
Figure 10:
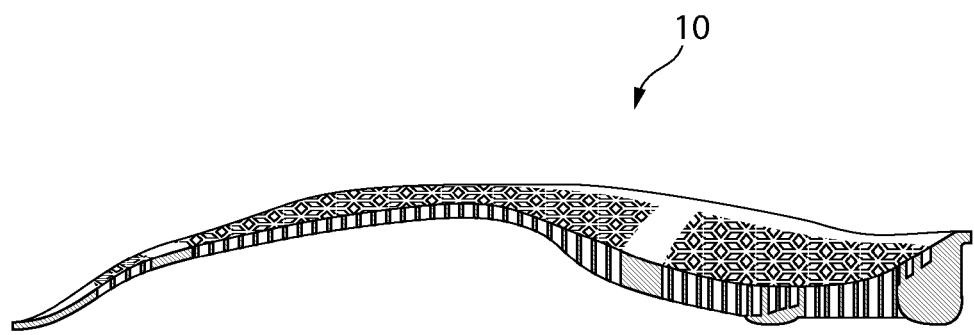
Figure 11:
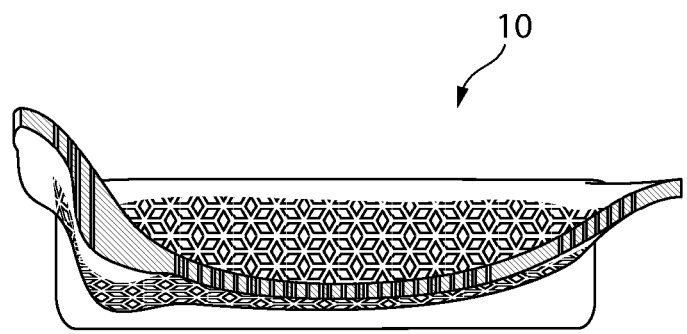

An area defined by the two end points of the line can now be extruded down from the surface of the Foot Orthotic, see FIG. 6. The thickness of this reinforcement is not constant and the line drawn represents the peak of the reinforcement. This can be 1-5 mm from the surface depending on the bespoke shape and functional requirements. The region to be reinforced is defined by the two circles which are connected. The distance from the line and its end points is used to "blend" the thickest part of the reinforcement with the Foot Orthotic shell. The distance from the line and the radius of the circles could be called the "diminishing distance".

This elevated area will then be blended to the rest of the shell over the diminishing distance, which is typically 5-15 mm but can be more or less depending on the bespoke shape and functional requirements. After this arch reinforcement feature is finished (see FIG. 7) the design process can continue.

There are also multiple ways to blend the elevated geometry to the shell. Examples of some of these are shown in images A to E in FIG. 8. In A, a general representation of the cross-section of the shell is shown together with a representation of the reinforcement, which in A is a smooth curve. In B the reinforcement has the same height as in A but this height is not "smoothened" and does not diminish until the edge of the reinforcement is reached. The edge of the reinforcement can go straight down or be perpendicular to the surface as in C. There may also be a gap in the reinforcement as presented in D. Furthermore, whichever of the above may be the case, the corners of the reinforcement can be rounded as in E.

Once the reinforcement is finished, the rest of the Foot Orthotic can be designed as described before. The perforations can go through the reinforce section. The use of perforations in this reinforced section does not alter the flexibility of the orthotic as much as it does in the thinner sections. The use of the perforations throughout the orthotic can be seen in the sectional views shown in FIGS. 9 to 11.

The reinforcement is designed in CAD and the Foot Orthotic with this feature is manufactured with additive manufacturing in a process such as SLS, FDM, SLA or any similar additive process. The additive manufacturing process uses a single material or a single mixture of materials to form the orthotic device. An example of a single material would be nylon but many other suitable materials may be used including mixtures which include nylon with other materials. The final orthotic can optionally be finished with a fabric material adhered to the top surface.

Referring particularly now to FIGS. 12 to 15, the Foot Orthotic may include one or more protrusions 42 extending from the lower surface 46 in particular the lower surface of the heel portion 44. The protrusion 42 is preferably in the form of a ring (see FIGS. 13 and 14) which extends slightly below (1-3 mm) the plane of the heel portion 44. The benefit of this heel reinforcement over a normal "flat" heel is that the additional ring structure will sink into the insole/midsole/sole of the shoe where the insole is used in. All of the user's weight is concentrated on this ring and it will usually make a permanent impression for itself and the Foot Orthotic will also sit in that impression and not move inside the shoe, which is advantageous to the user. To prevent the insole from sinking too far inside the shoe, the ring is filled with material by extending the Foot Orthotic shell until it reaches the "zero" plane of the heel portion.

If the ring is not extended below the "zero" plane, the shell under the heel will prevent it from sinking in. If the ring is extended but not filled, it will sink too far inside the shoe potentially damaging it.

It will be appreciated by persons skilled in the art that the above embodiments have been described by way of example only and not in any limitative sense, and that various alterations and modifications are possible without departure from the scope of the protection which is defined by the appended claims. For example slight variations on the embodiments described above are shown in the image of FIG. 44. Furthermore, variations in the shape of the perforations formed in the orthotic are possible and some examples of these are shown schematically in FIGS. 45 to 48.

The invention claimed is:

1. A method of making an orthotic, comprising the steps:
taking measurements relating to a foot;
creating a digital representation of an orthotic on a display device based on said measurements, the orthotic having a heel portion for supporting a heel of a person and a distal portion located in front of said heel portion, said distal portion being divided into a first and a second distal portion;
varying a thickness of the digital representation of the first and second distal portions such that said first distal portion is thinner than said second distal portion and said first distal portion includes no perforations formed therein and said second distal portion includes perforations; and
using additive manufacturing using a substantially uniform material or materials to create a physical version of the digital representation of the orthotic.

2. The method according to claim 1, further comprising substantially defining said first and second distal portions by an axial line extending from a distal edge of said orthotic towards said heel portion and a transverse line extending transverse to said axial line.

3. The method according to claim 2, wherein said axial line is located substantially between a first and second metatarsal of said measured foot.

4. The method according to claim 2, wherein said axial line is located between 10% and 30% across the width of the orthotic from the medial edge.

5. The method according to claim 2, wherein said transverse line is located substantially under the first metatarsal base of said measured foot.

6. The method according to claim 2, wherein said transverse line is located at around 40% of the length of the orthotic from the distal edge.

7. The method according to claim 2, wherein said transverse line is located substantially under the navicular bone of said measured foot.

8. The method according to claim 2, wherein said transverse line is located at around 60% of the length of the orthotic from the distal edge.

9. The method according to claim 2, wherein said transverse line is located adjacent said heel portion the first and second distal portions therefore extending along the whole length of the distal portion.

10. The method according to claim 2, wherein said transverse line is located at around 80% of the length of the orthotic from the distal edge.

11. The method according to claim 1, wherein the orthotic comprises an upper surface for engaging a foot and a lower surface for engaging an insole of a shoe, wherein said upper surface comprises a substantially continuous surface and the thickness of the first distal portion and the second distal portion are varied by varying the lower surface.

12. An orthotic comprising:
a heel portion for supporting a heel of a person; and
a distal portion located in front of said heel portion, said distal portion being divided into a first and a second distal portion wherein said first distal portion is thinner than said second distal portion and said first distal portion includes no perforations formed therein and said second distal portion includes perforations.

* * * * *